(12) United States Patent
Woods et al.

(10) Patent No.: US 8,748,503 B2
(45) Date of Patent: Jun. 10, 2014

(54) MACRO-PHOTOINITIATORS AND CURABLE COMPOSITIONS THEREOF

(71) Applicant: Henkel Corporation, Rocky Hill, CT (US)

(72) Inventors: John G. Woods, Farmington, CT (US); Roderick Coffey, Middletown, CT (US); Anthony F. Jacobine, Meriden, CT (US)

(73) Assignee: Henkel US IP LLC, Rocky Hill, CT (US)

( * ) Notice: Subject to any disclaimer, the term of this patent is extended or adjusted under 35 U.S.C. 154(b) by 0 days.

(21) Appl. No.: 13/623,982

(22) Filed: Sep. 21, 2012

(65) Prior Publication Data

US 2013/0018122 A1 Jan. 17, 2013

Related U.S. Application Data

(63) Continuation of application No. PCT/US2011/025153, filed on Feb. 17, 2011.

(60) Provisional application No. 61/316,190, filed on Mar. 22, 2010.

(51) Int. Cl.
- *B41J 2/16* (2006.01)
- *C08F 2/50* (2006.01)
- *C08F 2/46* (2006.01)
- *B29C 71/04* (2006.01)
- *A61L 2/08* (2006.01)
- *A61L 24/00* (2006.01)
- *C08G 61/04* (2006.01)

(52) U.S. Cl.
USPC .......... 522/35; 522/33; 522/6; 522/1; 522/71; 522/189; 522/184; 520/1

(58) Field of Classification Search
USPC ............. 522/35, 33, 6, 1, 71, 189, 184; 520/1
See application file for complete search history.

(56) References Cited

U.S. PATENT DOCUMENTS

| | | | |
|---|---|---|---|
| 4,102,945 A | 7/1978 | Gleave | |
| 4,105,715 A | 8/1978 | Gleave | |
| 6,458,864 B1 | 10/2002 | Asakura et al. | |
| 6,673,850 B1 * | 1/2004 | Yamato et al. | 522/33 |

FOREIGN PATENT DOCUMENTS

| | | | |
|---|---|---|---|
| KR | 100698799 | | 3/2007 |
| WO | 2009/137197 | * | 11/2009 |

OTHER PUBLICATIONS

Durmaz, Yasemin Yuksel et al, "Synthesis of block copolymers by combination of ATRP and photoiniferter processes", 2008, Polymer International, vol. 57, 1182-1187.*
International Search Report issued in connection with International Application No. PCT/US2011/025153 mailed Nov. 15, 2011.
Durmaz, Y. Y. et al. 'Synthesis of Block Copolymers by Combination of ATRP and Photoiniferter Processes.' In: Polym. Int., 2008, vol. 57, pp. 1182-1187. 1,2,6-12,16-25 See abstract, p. 1183, scheme 2. 3-5,13-15.
Durmaz, Y. Y. et al. 'N-Alkoxy Pyridinium Ion Terminated Polystyrenes: A Facile Route to Photoinduced Block Copolymerization.' In: J. Polym. Sci. Part A: Polym. Chem., 2007, vol. 45, pp. 423-428. 1,2,6-12,16-25 See abstract, pp. 424-425, schemes 2-3. 3-5,13-15.
Degirmenci, M. et al. 'Synthesis and Characterization of Macrophotoinitiators of Poly(epsilon-caprolactone) and Their Use in Block Copolymerization.' In: Macromolecules, 2002, vol. 35, pp. 8265-8270. 1-25 See the whole document.
M. Ciampolini, Inorg. Chem. 1966.

* cited by examiner

*Primary Examiner* — Ling-Siu Choi
*Assistant Examiner* — Jessica E Whiteley
(74) *Attorney, Agent, or Firm* — Steven C. Bauman

(57) ABSTRACT

Macro-photoinitiators having defined polymer chain structure are provided. The macro-photoinitiators are terminated with residues of thiol and/or hydroxyl functional photoinitiators. The macro-photoinitiators may be prepared by controlled radical polymerization methods, such as atom transfer radical polymerization and single electron transfer polymerization methods. Also provided are curable (e.g., photocurable) compositions that include the macro-photoinitiators of the present invention.

28 Claims, 5 Drawing Sheets

MACRO-PHOTOINITIATORS AND CURABLE COMPOSITIONS THEREOF

FIELD OF THE INVENTION

The present invention relates to macro-photoinitiators having defined polymer chain structure. The macro-photoinitiators are terminated with residues of thiol and/or hydroxyl functional photoinitiators. The present invention also relates to curable (e.g., photocurable) compositions that comprise such macro-photoinitiators.

BACKGROUND OF THE INVENTION

Compositions that are polymerized and/or crosslinked by exposure to actinic radiation (e.g., ultraviolet light) are used in a number of applications, such as coatings, adhesives, and the formation of molded articles (e.g., 3-dimensional shaped articles, such as gaskets and lenses). Such compositions typically include reactants having one or more ethylenically unsaturated groups that are radically polymerizable. Reactants having one or more ethylenically unsaturated groups that are radically polymerizable are not typically themselves rendered polymerizable by exposure to actinic radiation. The presence of an initiator that is activated by exposure to actinic radiation (typically referred to as a photoinitiator) is often required. Upon exposure to actinic radiation, the photoinitiator generates one or more initiator radicals that serve to initiate radical polymerization of the radically polymerizable reactants of the composition.

To achieve a sufficient level of initiation, an excess of photoinitiator is typically included in the curable composition. In many applications, photoinitiation is undertaken in the presence of oxygen, which inhibits radical polymerization, thus, requiring a further increase in the level of photoinitiator initially present within the curable composition. As such, the resulting cured material typically includes residual photoinitiator.

In addition to generating initiator radicals upon exposure to actinic radiation, photoinitiators typically also form or generate non-initiating co-products that that do not initiate radical polymerization. The photoinitiator itself, and the non-initiating co-products thereof typically have relatively low molecular weights, and as such, often volatilize and/or migrate from the resulting cured product. Such volatility and migration (or mobility) is generally undesirable due to, for example, related unpleasant odors and/or contamination of a surrounding matrix material (due to migration there-into). With photopolymerizable compositions used in food or medical applications, such as packaging adhesives, volatilization and mobility of residual photoinitiator and/or non-initiating co-products into the packaging matrix is typically undesirable as it may result in contamination of materials in contact with or contained within the packaging (e.g., food items or pharmaceuticals).

Polymeric photoinitiators, having higher molecular weights, have been developed in an attempt to minimize the volatility and/or migration associated with lower molecular weight photoinitiators. Polymeric photoinitiators are typically non-uniform with regard to, for example, polymer backbone structure, the terminal ends of the polymer, and/or polymer molecular weight, which may lead to variable properties and reactivities of the polymeric photoinitiator.

It would be desirable to develop new photoinitiators having reduced or minimal volatility and/or migration associated therewith. In addition, it would be desirable that such newly developed photoinitiators also have consistent properties and reactivities.

SUMMARY OF THE INVENTION

In accordance with the present invention, there is provided a macro-photoinitiator comprising a polymer chain structure represented by the following general formula (I),

$$\Phi\text{-}[[\text{-}(M)_p\text{-}]_x\text{-}Y\text{-}L\text{-}PI]_z \qquad (I)$$

wherein, $\Phi$ is a residue of a polymerization initiator,

M is a residue of at least one ethylenically unsaturated radically polymerizable monomer, p represents an average number of monomer residues occurring in a block of monomer residues, p, x, and z are each individually selected such that said macro-photoinitiator has a number average molecular weight of at least 400, p is, independently for each x, an integer from 1 to 1000, x is, independently for each z, an integer from 1 to 20, z is at least 1, Y, independently for each z, is selected from S (i.e., represents a sulfide linkage) and O (i.e., represents an ether linkage), L, independently for each z, is a bond or a divalent linking group comprising at least one divalent moiety selected from the group consisting of divalent organic moieties, divalent inorganic moieties, and combinations thereof, and PI, independently for each z, represents a photoinitiator residue. The photoinitiator residue (PI) comprises a photoactive (or photoinitiator) moiety.

In further accordance with the present invention, there is provided a curable composition comprising: a macro-photoinitiator as described above; and at least one reactant comprising at least one ethylenically unsaturated radically polymerizable group.

There is also provided, in accordance with the present invention, a method of forming an article, which comprises: providing the curable composition described above; and exposing the curable composition to actinic radiation in an amount at least sufficient to result in cure of the curable composition and formation of the article (e.g., a molded gasket).

There is further provided, in accordance with the present invention, an article (e.g., a gasket) that is formed by exposing the curable composition described above to actinic radiation in an amount at least sufficient to result in cure of the curable composition (i.e., resulting in formation of a 3 dimensional crosslink network comprising covalent bonds).

As used herein and in the claims, unless otherwise indicated, molecular weights, such as "number average molecular weights," are determined by gel permeation chromatography using appropriate polymer standards, such as poly (methylmethacrylate) (PMMA) standards.

As used herein and in the claims, the term "(meth)acrylate" and similar terms, such as "esters of (meth)acrylic acid" means acrylates and/or methacrylates.

As used herein and in the claims, the term "actinic radiation" means electromagnetic radiation that is capable of transforming a photoinitiator from an inactive form to an active form that is capable of initiating radical polymerization, and includes, but is not limited to, infrared light, visible light, ultraviolet (UV) light, electron beam radiation, and concurrent and/or sequential combinations thereof.

As used herein and in the claims, the term "photoinitiator" and similar terms, such as macro-photoinitiator, means a material that is transformed from an inactive form to an active form that is capable of initiating radical polymerization upon exposure to actinic radiation.

As used herein, the term "polymer" is meant to refer to both homopolymers, i.e., polymers made from a single monomer species, and copolymers, i.e., polymers made from two or more monomer species.

Unless otherwise indicated, all ranges disclosed herein are to be understood to encompass any and all subranges subsumed therein. For example, a stated range of "1 to 10" should be considered to include any and all subranges between (and inclusive of) the minimum value of 1 and the maximum value of 10; that is, all subranges beginning with a minimum value of 1 or more and ending with a maximum value of 10 or less, e.g., 1 to 6.1, 3.5 to 7.8, 5.5 to 10, etc.

Other than in the operating examples, or where otherwise indicated, all numbers expressing quantities of ingredients, reaction conditions, and so forth used in the specification and claims are to be understood as modified in all instances by the term "about."

DETAILED DESCRIPTION OF THE INVENTION

Figure 1:
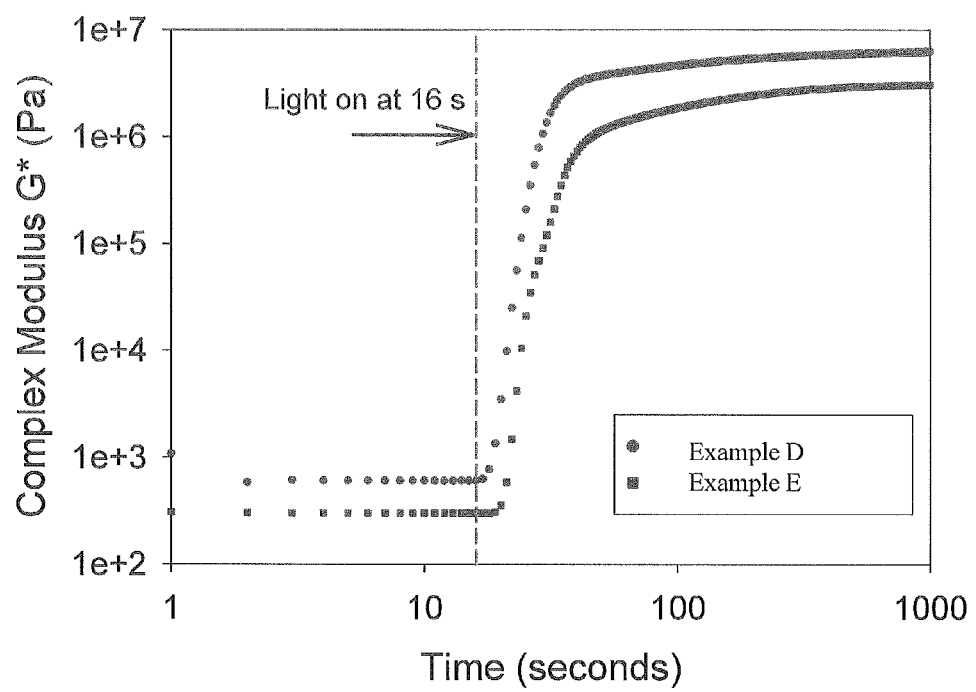
FIG. 1 is a graphical representation of a plot of complex modulus G* as a function of time during UV curing of compositions according to Examples D and E.

Macro-photoinitiators of the present invention comprise a residue of an initiator, which is designated by the symbol $\Phi$ in formula (I). The initiator initiates formation of at least a portion of the macro-photoinitiator. Typically, the initiator initiates polymerization of ethylenically unsaturated radically polymerizable monomers, and is a polymerization initiator. In an embodiment of the present invention, the initiator initiates controlled radical polymerization, and includes a transferable group (e.g., a radically transferable group) as discussed in further detail below. The residue of the initiator, $\Phi$, may be selected from linear or branched aliphatic compounds, cycloaliphatic compounds, heterocyclic compounds, aryl compounds, heteroaryl compounds, aralkyl compounds, sulfonyl compounds, sulfenyl compounds, esters of carboxylic acids, polymeric compounds, and mixtures or combinations thereof. The residue of the initiator may also be substituted with functional groups (e.g., oxyranyl groups, such as glycidyl groups, or active hydrogen groups, such as hydroxyl groups, primary amine groups, and secondary amine groups).

Examples of linear or branched aliphatic compounds from which the residue of the initiator may be selected include, but are not limited to, linear or branched $C_1$-$C_{20}$ alkyl groups (e.g., linear or branched $C_1$-$C_{10}$ alkyl); linear or branched $C_2$-$C_{20}$ alkenyl groups (e.g., linear or branched $C_2$-$C_{10}$ alkenyl); and linear or branched $C_2$-$C_{20}$ alkynyl groups (e.g., linear or branched $C_2$-$C_{10}$ alkynyl). Representative alkyl groups include, but are not limited to, methyl, ethyl, propyl, isopropyl, butyl, isobutyl, sec-butyl, test-butyl, pentyl, neopentyl, hexyl, heptyl, octyl, nonyl, and decyl. Representative alkenyl groups include, but are not limited to, vinyl, allyl, and propenyl. Representative alkynyl groups include, but are not limited to, ethynyl, 1-propynyl, 2-propynyl, 1-butynyl, and 2-butynyl.

As used herein and in the claims, recitations of linear or branched $C_1$-$C_x$ groups, in which x is greater than the first recited subscript, such as at least 2 (e.g., linear or branched $C_1$-$C_{20}$ alkyl groups), and similar recitations, such as $C_1$-$C_x$ linear or branched groups, means linear $C_1$-$C_x$ groups (e.g., linear $C_1$-$C_{20}$ alkyl groups) and branched $C_3$-$C_x$ groups (e.g., branched $C_3$-$C_{20}$ alkyl groups). Similarly, as used herein and in the claims, recitations of linear or branched $C_2$-$C_y$ groups, in which y is greater than the first recited subscript, such as at least 3 (e.g., linear or branched $C_2$-$C_{20}$ alkenyl groups, or linear or branched $C_2$-$C_{20}$ alkynyl groups), and similar recitations, such as $C_2$-$C_y$ linear or branched groups, means linear $C_2$-$C_y$ groups (e.g., linear $C_2$-$C_{20}$ alkenyl groups, or linear $C_2$-$C_{20}$ alkynyl groups), and branched $C_3$-$C_y$ groups (e.g., branched $C_3$-$C_{20}$ alkenyl groups, or branched $C_3$-$C_{20}$ alkynyl groups).

Examples of cycloaliphatic compounds from which the residue of the initiator may be selected include, but are not limited to, $C_3$-$C_{12}$ cycloalkyl groups (e.g., $C_3$-$C_{10}$ cycloalkyl groups). Representative cycloalkyl groups include, but are not limited to, cyclopropyl, cyclobutyl, cyclopentyl, cyclohexyl, and cyclooctyl.

Examples of heterocyclic compounds from which the residue of the initiator may be selected include, but are not limited to, $C_3$-$C_{12}$ heterocycloalkyl groups (having at least one hetero atom in the cyclic ring). Representative heterocycloalkyl groups include, but are not limited to, tetrahydrofuranyl, tetrahydropyranyl, and piperidinyl.

Aryl compounds from which the residue of the initiator may be selected include, but are not limited to, $C_5$-$C_{18}$ aryl groups (including polycyclic aryl groups) (e.g., $C_5$-$C_{10}$ aryl groups). Representative aryl groups include, but are not limited to, phenyl, naphthyl, and anthracenyl groups.

Heteroaryl compounds from which the residue of the initiator may be selected include, but are not limited to, $C_5$-$C_{18}$ heteroaryl groups (having at least one hetero atom in the aromatic ring, and including polycyclic heteroaryl compounds). Representative heteroaryl groups include, but are not limited to, furanyl, pyranyl, and pyridinyl.

Aralkyl compounds from which the residue of the initiator may be selected include, but are not limited to, $C_6$-$C_{24}$ aralkyl groups (e.g., $C_6$-$C_{10}$ aralkyl groups). Representative aralkyl groups include, but are not limited to, benzyl (e.g., $C_6H_5$—$CH_2$—), and phenethyl (e.g., $C_6H_5$—$CH_2CH_2$— and $C_6H_5$—$CH(CH_3)$—).

Sulfonyl compounds, from which the residue of the initiator may be selected, include those represented by the following general formula 1,

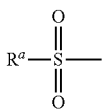

(I)

In general, formula (I), $R^a$ may be selected from hydrogen, linear or branched aliphatic compounds, cycloaliphatic compounds, heterocyclic compounds, aryl compounds, heteroaryl compounds. Classes and examples of linear or branched aliphatic compounds, cycloaliphatic compounds, heterocyclic compounds, aryl compounds, and heteroaryl compounds include those described above. In an embodiment, the sulfonyl compound is selected from methane sulfonyl ($R^a$ being methyl) and p-toluenesulfonyl ($R^a$ being p-toluenyl).

Sulfenyl compounds from which the residue of the initiator may be selected include those represented by the following general formula (m), $$R^b\text{—S—}\quad(\text{m})$$

In general, formula (m), $R^b$ may be selected from linear or branched aliphatic compounds, cycloaliphatic compounds, and heterocyclic compounds, aryl compounds, and heteroaryl compounds. Classes and examples of linear or branched aliphatic compounds, cycloaliphatic compounds, heterocyclic compounds, aryl compounds, and heteroaryl compounds include those described above. In an embodiment, the sulfenyl compound is selected from linear or branched $C_1$-$C_5$ alkyl sulfenyl, $C_3$-$C_6$ cycloalkyl sulfenyl and benzene sulfenyl.

Esters of carboxylic acids from which the residue of the initiator may be selected include those represented by the following general formulas (n) and (o),

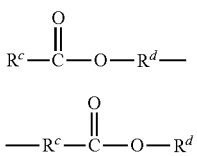

In general, formulas (n) and (o) divalent $R^c$ and divalent $R^d$ may each be independently selected from linear or branched aliphatic compounds, cycloaliphatic compounds, heterocyclic compounds, aryl compounds, heteroaryl compounds; and monovalent $R^c$ of general formula (n) and monovalent $R^d$ of general formula (o) may each be further selected from hydrogen. Classes and examples of linear or branched aliphatic compounds, cycloaliphatic compounds, heterocyclic compounds, aryl compounds, and heteroaryl compounds include those described above. Esters of carboxylic acids from which the residue of the initiator may be selected, also include diesters of dicarboxylic acids, such as di($C_1$-$C_6$ alkyl) malonate and di($C_1$-$C_6$ alkyl) adipate. An example of an ester of a carboxylic acid from which the residue of the initiator may be selected includes $C_1$-$C_6$-alkyl 2-isobutyrate, e.g., —($CH_3CH_2$)—CH—C(O)—O—($C_1$-$C_6$ alkyl).

Polymeric compounds (including oligomeric compounds) from which the residue of the initiator may be selected include, but are not limited to, polymers prepared by living and non-living polymerization, and may be referred to as residues of macroinitiators, which will be discussed in further detail herein. Examples of polymeric compounds from which the residue of the initiator may be selected include, but are not limited to, polyolefins, polystyrenes, poly(meth)acrylates, polyacrylamides, polymethacrylamides, poly(N-vinylamides), poly(acrylonitrile), polyurethanes, polyesters, polyethers, and polycarbonates.

Residue M of the polymer chain structure represented by general formula (I) is derived from at least one ethylenically unsaturated radically polymerizable monomer. As used herein and in the claims, "ethylenically unsaturated radically polymerizable monomer" and similar terms are meant to include vinyl monomers, allylic monomers, olefins, and other ethylenically unsaturated monomers that are radically polymerizable.

Classes of vinyl monomers from which M may be derived include, but are not limited to, (meth)acrylates, vinyl aromatic monomers, vinyl halides, and vinyl esters of carboxylic acids. As used herein and in the claims, by "(meth)acrylate" and similar terms is meant both methacrylates and acrylates. Typically, residue M is derived from at least one of alkyl (meth)acrylates having from 1 to 20 carbon atoms in the alkyl group. Examples of alkyl (meth)acrylates having from 1 to 20 carbon atoms in the alkyl group from which residue M may be derived include, but are not limited to, methyl(meth)acrylate, ethyl(meth)acrylate, 2-hydroxyethyl(meth)acrylate, propyl (meth)acrylate, 2-hydroxypropyl(meth)acrylate, isopropyl (meth)acrylate, butyl(meth)acrylate, isobutyl(meth)acrylate, tert-butyl(meth)acrylate, 2-ethylhexyl(meth)acrylate, lauryl (meth)acrylate, isobornyl(meth)acrylate, cyclohexyl(meth) acrylate, and 3,3,5-trimethylcyclohexyl(meth)acrylate.

Residue M may also be selected from monomers having more than one ethylenically unsaturated radically polymerizable group, such as more than one (meth)acrylate group, for example, (meth)acrylic anhydride, diethyleneglycol bis ((meth)acrylate) and trimethylolpropane tris((meth)acrylate). Residue M may also be selected from monomers (e.g., alkyl(meth)acrylates) containing radically transferable groups, which can act as branching monomers in controlled radical polymerization processes, for example, 2-(2-bromopropionoxy)ethyl acrylate.

Examples of vinyl aromatic monomers from which M may be derived include, but are not limited to, styrene, p-chloromethylstyrene, divinyl benzene, vinyl naphthalene, and divinyl naphthalene. Vinyl halides from which M may be derived include, but are not limited to, vinyl chloride and vinylidene fluoride. Vinyl esters of carboxylic acids from which M may be derived include, but are not limited to, vinyl acetate, vinyl butyrate, vinyl 3,4-dimethoxybenzoate, and vinyl benzoate.

As used herein and in the claims, by "olefin" and like terms is meant unsaturated aliphatic hydrocarbons having one or more double bonds, such as obtained by cracking petroleum fractions. Specific examples of olefins from which M may be derived include, but are not limited to, propylene, 1-butene, 1,3-butadiene, isobutylene, and diisobutylene.

As used herein and in the claims, by "allylic monomer(s)" is meant monomers containing substituted and/or unsubstituted allylic functionality, i.e., one or more radicals represented by the following general formula V, $$H_2C=C(R_{10})-CH_2-\quad(V)$$

wherein $R_{10}$ is hydrogen, halogen, or a $C_1$ to $C_4$ alkyl group. Typically, $R_{10}$ is hydrogen or methyl and consequently general formula V represents the unsubstituted (meth)allyl radical. Examples of allylic monomers include, but are not limited to, (meth)allyl alcohol, (meth)allyl ethers, such as methyl (meth)allyl ether, allyl esters of carboxylic acids, such as (meth)allyl acetate, (meth)allyl butyrate, (meth)allyl 3,4-dimethoxybenzoate, and (meth)allyl benzoate.

Other ethylenically unsaturated radically polymerizable monomers from which M may be derived include, but are not limited to, cyclic anhydrides (e.g., maleic anhydride, 1-cyclopentene-1,2-dicarboxylic anhydride and itaconic anhydride) esters of acids that are unsaturated but do not have α,β-ethylenic unsaturation, (e.g., methyl ester of undecylenic acid), diesters of ethylenically unsaturated dibasic acids, (e.g., diethyl maleate, acrylonitrile; methacrylonitrile), N,N-di($C_1$-$C_6$ alkyl)-(meth)acrylamides, and N-vinylamides.

Residue M may also be derived from monomers having epoxy (i.e., epoxide or oxirane) functionality, thus providing the macro-photoinitiator with pendent epoxy functionality. The pendent epoxy functionality may be used to further immobilize the macro-photoinitiator within a cured composition or article prepared from a curable composition containing the macro-photoinitiator, as will be discussed in further detail herein. Examples of epoxy functional monomers from which residue M may be derived, include but are not limited to, glycidyl(meth)acrylate, 3,4-epoxycyclohexylmethyl (meth)acrylate, 2-(3,4-epoxycyclohexyl)ethyl (meth)acrylate, and allyl glycidyl ether. Alternatively, epoxy functionality may be incorporated into the macro-photoinitiator by post-reaction, such as by preparing a macro-photoinitiator having hydroxyl groups pendent from the polymer backbone thereof, and then reacting at least some of the pendent hydroxyl groups with epichlorohydrin.

In an embodiment, monomer residue M is derived from at least one of alkyl(meth)acrylates having from 1 to 20 carbon atoms in the alkyl group (e.g., ethyl acrylate, 2-methoxyethyl acrylate and/or n-butyl acrylate), vinyl aromatic monomers (e.g., styrene), vinyl halides, vinyl esters of carboxylic acids, olefins, acrylonitrile, methacrylonitrile, one or more N,N-di ($C_1$-$C_6$ alkyl)-(meth)acrylamides, and mixtures thereof.

Subscript p of the general polymer chain structure represented by formula (I) represents an average number of monomer residues occurring in a block of monomer residues (or an M block of residues). Subscript x represents the number of segments of M blocks (i.e., x-segments). Subscript z represents the number of polymer chain segments that are attached to the residue of the initiator, Φ. Subscript p may each be the same or different for each x-segment. Subscript x may be the same or different for each z (or z-polymer chain segment). Accordingly each polymer chain segment (or z-polymer chain segment) that is attached to initiator residue Φ, may be the same or different, when z is greater than 1.

Subscript p may be, independently for each x, an integer from 1 to 5000, or 1 to 1000, or 5 to 500, or 10 to 200. In an embodiment, subscript p is, independently for each x, an integer from 2 to 20. Subscript p may be, independently for each z, an integer from 1 to 20, or 2 to 15, or 3 to 10.

Subscript z is equal to the number of polymer chain segments that are attached to initiator residue Φ. As such, subscript z is at least 1, and may have a wide range of values. In the case of comb or graft polymers, in which for example, initiator residue Φ is a residue of a macroinitiator having several pendent radically transferable groups, z can have a value in excess of 10, for example 50, 100, or 1000. Typically, z is less than or equal to 10, such as less than or equal to 5. Subscript z may be from 1 to 10, or from 1 to 5. In an embodiment, subscript z is 1 or 2.

With further reference to general formula (I), M represents one or more types of monomer residues, and p represents the average total number of M residues occurring per block of M residues (M-block) within an x-segment. Within each x-segment, the -(M)$_p$- portion of general formula (I) represents: (1) a homoblock of a single type of M residue; (2) an alternating block of two types of M residues; (3) a polyblock of two or more types of M residues (e.g., a random block of two or more types of M residues); or (4) a gradient block of two or more types of M residues.

For purposes of illustration, when an M-block is prepared from, for example, 10 moles of methyl methacrylate, the -(M)$_p$- portion of general formula (I) represents (within an x-segment) a homoblock of 10 residues of methyl methacrylate. In the case where the M-block is prepared from, for example, 5 moles of methyl methacrylate and 5 moles of butyl methacrylate, the -(M)$_p$- portion of general formula (I) represents (within an x-segment), depending on the conditions of preparation, as is known to one of ordinary skill in the art: (a) a diblock of 5 residues of methyl methacrylate and 5 residues of butyl methacrylate having a total of 10 residues (i.e., p=10); (b) a diblock of 5 residues of butyl methacrylate and 5 residues of methyl methacrylate having a total of 10 residues; (c) an alternating block of methyl methacrylate and butyl methacrylate residues beginning with either a residue of methyl methacrylate or a residue of butyl methacrylate, and having a total of 10 residues; or (d) a gradient block of methyl methacrylate and butyl methacrylate residues beginning with either residues of methyl methacrylate or residues of butyl methacrylate, and having a total of 10 residues.

Subscripts p, x, and z are each independently selected such that the macro-photoinitiator has a number average molecular weight of at least 400. The macro-photoinitiator may, for example, have a number average molecular weight of at least 400, or at least 500, or at least 800, or at least 1,500. The macro-photoinitiator may, for example, have a number average molecular weight of less than or equal to 500,000, or less than or equal to 100,000, or less than or equal to 80,000, or less than or equal to 50,000, or less than or equal to 35,000. The number average molecular weight of the macro-photoinitiator may range between any combination of these upper and lower values, inclusive of the recited values. For example, the number average molecular weight of the macro-photoinitiator may be from: 400 to 500,000; 400 to 100,000; 500 to 100,000; 800 to 80,000; 1,500 to 50,000; or 1,500 to 35,000, inclusive of the recited values.

The macro-photoinitiator of the present invention may have any suitable polydispersity index (PDI). Typically, the macro-photoinitiator has a PDI of less than or equal to 4.0, for example, less than or equal to 3.5, or less than or equal to 3.0. In an embodiment, the macro-photoinitiator has a PDI of less than or equal to 2.5, or less than or equal to 1.8 (e.g., 1.5). As used herein, and in the claims, "polydispersity index" is determined from the following equation: (weight average molecular weight (Mw)/number average molecular weight (Mn)). A monodisperse polymer has a PDI of 1.0. Further, as used herein, Mn and Mw are determined from gel permeation chromatography using appropriate polymer standards, such as, poly(methylmethacrylate) (PMMA) standards.

The symbol L of the polymer chain structure represented by general formula (I) may be a bond or a divalent linking group that includes at least one divalent moiety selected from one or more divalent organic moieties and/or one or more divalent inorganic moieties. The divalent linking group L may include a plurality of divalent organic moieties and a plurality of divalent inorganic moieties. As used herein and in the claims, the term "divalent organic moieties/moiety" and similar terms, such as "divalent organic group(s)" may also be described as "divalent hydrocarbylene moieties." More particularly, as used herein and in the claims, the term "divalent organic moieties/moiety" and similar terms, such as "divalent organic group(s)" means substituted or unsubstituted linear or branched $C_1$-$C_{20}$ alkylene, substituted, or unsubstituted linear or branched $C_2$-$C_{20}$ alkenylene, substituted or unsubstituted, linear or branched $C_2$-$C_{10}$ alkynyl, substituted or unsubstituted $C_3$-$C_{10}$ cycloalkylene, substituted or unsubstituted $C_3$-$C_{10}$ heterocycloalkylene (having at least one hetero atom in the cyclic ring), substituted or unsubstituted arylene (e.g., $C_6$-$C_{18}$ aryl, including polycyclic arylene groups), substituted or unsubstituted heteroarylene (having at least one hetero atom in the cyclic arylene ring or rings).

With regard to the divalent organic moieties from which the divalent linking group L may be selected, representative and non-limiting examples of divalent alkylene groups include, but are not limited to, methylene (—$CH_2$—), ethylene (—$CH_2CH_2$—), propylene (—$CH_2CH_2CH_2$—), isopropylene (e.g., —$CH_2CH(CH_3)$—), butylene (—$CH_2CH_2CH_2CH_2$—), isobutylene, sec-butylene, tert-butylene, pentylene, neopentylene, hexylene, heptylene, octylene, nonylene, and decylene. Representative and non-limiting examples of divalent alkenylene groups include, but are not limited to, vinylene (—CH═CH—) and propenylene (e.g., —$C(CH_3)$═CH—). Representative and non-limiting examples of divalent alkynylene groups include, but are not limited to, ethynylene (—C≡C—), propynylene (—C≡C—$CH_2$—), and butynylene (e.g., —C≡C—$CH(CH_2)$—). Representative and non-limiting examples of divalent cycloalkylene groups include, but are not limited to, cyclopropylene, cyclobutylene, cyclopentylene, cyclohexylene, and cyclooctylene. Representative and non-limiting examples of divalent heterocycloalkylene groups include, but are not limited to, tetrahydrofuranylene, tetrahydropyranylene, and piperidinylene. Representative and non-limiting examples of divalent arylene groups include, but are not limited to, phenylene, naphthylene, and anthracenylene. Representative and non-limiting examples of divalent heteroarylene groups include, but are not limited to, furanylene, pyranylene, and pyridinylene. Representative and non-limiting examples of divalent aralkylene groups include, but are not limited to, benzylene and phenethylene.

The term "substituted" with regard to the various divalent moieties from which the divalent organic moiety may be selected means that at least one of the substitutable hydrogens of the divalent organic moiety is substituted with another group. For example, a substituted $C_1$-$C_{20}$ alkylene group may be substituted with at least one substituent selected from alkenyl groups, alkynyl groups, cycloalkyl groups, heterocycloalkyl groups, aryl groups, and heteroaryl groups. Examples of substituents of the substituted divalent organic moieties include, but are not limited to, alkyl groups (e.g., methyl, ethyl, propyl, isopropyl, butyl, isobutyl, sec-butyl, tert-butyl, pentyl, neopentyl, hexyl, heptyl, octyl, nonyl and decyl) alkenyl groups (e.g., vinyl, allyl and propenyl) alkynyl groups (e.g., ethynyl, 1-propynyl, 2-propynyl, 1-butynyl, and 2-butynyl) cycloalkyl groups (e.g., cyclopropyl, cyclobutyl, cyclopentyl, cyclohexyl, and cyclooctyl) heterocycloalkyl groups (e.g., tetrahydrofuranyl, tetrahydropyranyl, and piperidinyl) aryl groups (e.g., phenyl, biphenyl, naphthyl, and anthracenyl) arakyl groups (e.g., benzyl and phenethyl), and heteroaryl groups (e.g., furanyl, pyranyl, and pyridinyl) halo or halogen groups (e.g., chloro, bromo, fluoro and iodo) ketones (e.g., hydrocarbyl ketones), carboxylic acid esters (e.g., hydrocarbyl carboxylates), hydroxyl, thiol, amino groups (e.g., —$NH_2$), ethers (e.g., hydrocarbyl ethers), thio ethers (e.g., hydrocarbyl thio ethers), and combinations thereof.

The term "unsubstituted" with regard to the various divalent moieties from which the divalent organic moiety may be selected means that none of the substitutable hydrogens of the divalent organic moiety are substituted with another group (e.g., a halogen).

The divalent inorganic linking group, of the divalent linking group L of the macro-photoinitiator represented by general formula (I), may be selected from, for example, at least one of: —O—; —C(O)—; —C(O)—O—; —O—C(O)—O—; and combinations thereof. Additional examples of divalent inorganic linking groups from which the divalent linking group L may be selected, include but are not limited to: —C(O)—NH—; —NH—C(O)—O—; —NH—C(O)—S—; —NH—C(S)—O—; and —NH—C(S)—S—.

The symbol Y of general formula (I) represents: a sulfur group (S), and more particularly, a sulfide linkage (or divalent sulfide linkage) i.e., —S—; or an oxygen group (O), and more particularly an ether linkage (i.e., —O—). In an embodiment of the present invention, the combination of the divalent linkage, —Y—, and the divalent linking group L, -L- (i.e., —Y-L-) may be represented by the following general formula (IIIa),

(IIIa)

In general formula (IIIa), $R_6$ is a divalent organic moiety, and $R_7$ is a bond or a divalent organic moiety. The divalent organic moieties from which $R_6$ and $R_7$ may each be independently selected include those divalent organic moieties as described previously herein with regard to the divalent linking group L of general formula (I). In a particular embodiment, Y is S and —Y-L- of general formula (I) accordingly is —S-L-, and the combination of the divalent sulfide linkage, —S—, and the divalent linking group L, -L- (i.e., —S-L-) may be represented by the following general formula (IIIb),

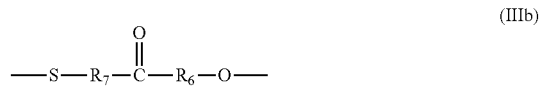

(IIIb)

In general formula (IIIb), $R_6$ and $R_7$ are as described with regard to general formula (IIIa).

The divalent organic moieties from which $R_6$ and $R_7$ may each be independently selected include, for example, substituted or unsubstituted linear or branched $C_1$-$C_{20}$ alkylene, substituted or unsubstituted linear or branched $C_2$-$C_{20}$ alkenylene, substituted or unsubstituted linear or branched $C_2$-$C_{10}$ alkynyl, substituted or unsubstituted $C_3$-$C_{10}$ cycloalkylene, substituted or unsubstituted $C_3$-$C_{10}$ heterocycloalkylene (having at least one hetero atom in the cyclic ring), substituted or unsubstituted arylene (e.g., $C_6$-$C_{18}$ aryl, including polycyclic arylene groups), and substituted or unsubstituted heteroarylene (having at least one hetero atom in the cyclic arylene ring or rings). The terms substituted and unsubstituted being as described previously herein with regard to the divalent linking group L of formula (I).

In an embodiment, $R_6$ and $R_7$ of general formula (III) are each independently selected from divalent linear or branched $C_1$-$C_6$ alkylene. Examples of divalent linear or branched $C_1$-$C_6$ alkylene groups from which $R_6$ and $R_7$ may each be independently selected, include but are not limited to, methylene (—$CH_2$—), ethylene (—$CH_2CH_2$—), propylene (—$CH_2CH_2CH_2$—), isopropylene (e.g., —$CH_2CH(CH_3)$—), butylene (—$CH_2CH_2CH_2CH_2$—), isobutylene, sec-butylene, tert-butylene, pentylene, neopentylene, and hexylene.

The symbol PI of general formula (I) represents a residue of a photoinitiator. The residue of the photoinitiator (PI) comprises a photoactive moiety. The photoinitiator residue may be selected from, for example, anthraquinone residues, for example, represented by the following general formula (a),

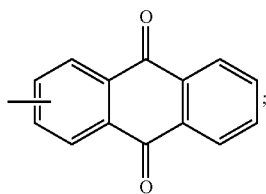

(a)

thioxanthone residues, for example, represented by the following general formula (b),

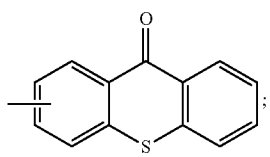

(b)

triazine residues, for example, represented by the following general formula (c),

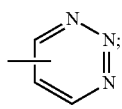

(c)

and fluorenone residues, for example, represented by the following general formula (d),

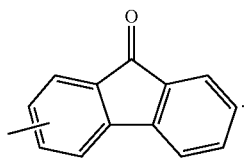

(d)

In addition, the photoinitiator residue PI may be selected from photoinitiator residues represented by the following general formula (II),

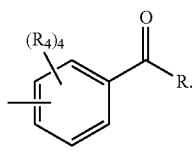

With the photoinitiator residue represented by general formula (II), R may be: aryl; aryl substituted with at least one substituent selected from linear or branched $C_1$-$C_{20}$ alkyl, halogen (e.g., fluoro, chloro, bromo and/or iodo) and combinations thereof; $C_3$-$C_{12}$ cycloalkyl optionally substituted with at least one substituent selected from linear or branched $C_1$-$C_{20}$ alkyl, halogen (e.g., fluoro, chloro, bromo and/or iodo), hydroxyl and combinations thereof; or —$CR_1R_2R_3$.

Examples of aryl groups from which R may be selected include, but are not limited to, phenyl, biphenyl, naphthyl, and anthracenyl. Examples of $C_1$-$C_{20}$ alkyl groups that may be substituents of the aryl groups, include but are not limited to, methyl, ethyl, propyl, isopropyl, butyl, isobutyl, sec-butyl, tert-butyl, pentyl, neopentyl, hexyl, heptyl, octyl, nonyl, decyl, undecyl, dodecyl, tridecyl, tetradecyl, pentadecyl, hexadecyl, heptadecyl, octadecyl, nonadecyl, and icosanyl. Examples of $C_3$-$C_{12}$ cycloalkyls from which R of general formula (III) may be selected include, but are not limited to, cyclopropyl, cyclobutyl, cyclopentyl, cyclohexyl, cycloheptyl, cyclooctyl, cyclononyl, cyclodecyl, cycloundecyl, and cyclododecyl. Typically, cycloalkyls from which R may be selected include cyclopentyl, cyclohexyl, and cycloheptyl.

The $R_1$, $R_2$, and $R_3$ groups of —$CR_1R_2R_3$, of R of general formula (II), may each be individually and independently selected from: hydrogen; hydroxyl; aryl; aryl substituted with at least one substituent selected from $C_1$-$C_{20}$ alkyl, halogen, and combinations thereof; $C_1$-$C_{20}$ hydroxylalkyl; $C_1$-$C_{20}$ alkoxy; $C_3$-$C_{12}$ cycloalkyl; and —$C(O)$—$R_5$ wherein $R_5$ is aryl or aryl substituted with at least one substituent selected from $C_1$-$C_{20}$ alkyl, halogen, and combinations thereof. The aryl groups and alkyl substituents thereof, and cycloalkyl groups may be selected from those classes and examples as described above with regard to R. The $C_1$-$C_{20}$ hydroxylalkyl groups from which $R_1$, $R_2$, and $R_3$ may each be independently selected, may have one or more hydroxyl groups, which may be located pendently alone or terminally on the alkyl group. The $C_1$-$C_{20}$ alkoxy groups from which $R_1$, $R_2$, and $R_3$ may each be independently selected, may include one or more ether oxygens, and typically one ether oxygen.

The $R_4$ groups of general formula (II) may in each instance be independently selected from hydrogen, halogen, linear or branched $C_1$-$C_{20}$ alkyl, $C_3$-$C_{12}$ cycloalkyl, and aryl. The alkyl, cycloalkyl, and aryl groups may be selected from those classes and examples as described above with regard to R.

For purposes of non-limiting illustration, when $R_4$ is hydrogen, and R is phenyl, the photoinitiator residue represented by general formula (II) is a residue of benzophenone, which may be represented by the following general formula (e),

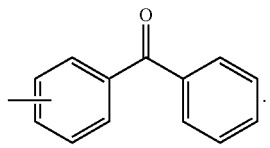

(e)

When, for example, $R_4$ is hydrogen, and R is methyl, the photoinitiator residue represented by general formula (II) is a residue of acetophenone, which may be represented by the following general formula (f-1),

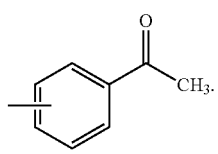

(f-1)

When, for example, $R_4$ is hydrogen, and R is $CR_1R_2R_3$ in which $R_1$ is hydrogen, and $R_2$ and $R_3$ are each ethoxy (—$OCH_2CH_3$), the photoinitiator residue represented by general formula (II) is a residue of diethoxy acetophenone, which may be represented by the following general formula (f-2),

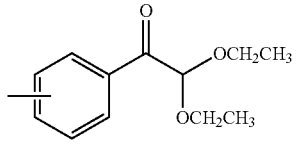
(f-2)

When, for example, $R_4$ is hydrogen, and R is —C(O)—$R_5$ and $R_5$ is phenyl, the photoinitiator residue represented by general formula (II) is a residue of benzil, which may be represented by the following general formula (g),

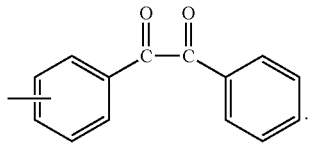
(g)

For purposes of further non-limiting illustration, when $R_4$ is hydrogen, and R is a residue of benzyl alcohol, the photoinitiator residue represented by general formula (II) is a residue of benzoin, which may be represented by the following general formula (h-1),

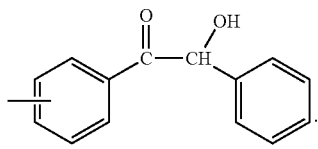
(h-1)

When $R_4$ is hydrogen, and R is $CR_1R_2R_3$ in which $R_1$ is hydrogen, and $R_2$ is phenyl and $R_3$ is ethoxy (—$OCH_2CH_3$), the photoinitiator residue represented by general formula (II) is a residue of ethyl benzoin ether, which may be represented by the following general formula (h-2),

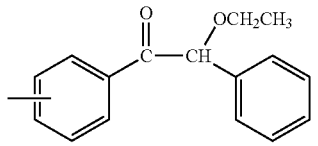
(h-2)

For example, when $R_4$ is hydrogen, and R is a hydroxyl alkyl group, the photoinitiator residue represented by general formula (II) is a residue of hydroxylalkylphenone, which may be represented by the following general formula (i),

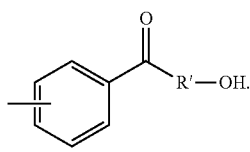
(i)

The R' group of general formula (I) is a linear or branched $C_1$-$C_{20}$ alkyl group, such as methyl or ethyl.

In addition, when $R_4$ is hydrogen, and R is cyclohexyl, the photoinitiator residue represented by general formula (II) is a residue of phenyl-cyclohexyl ketone, which may be represented by the following general formula (j-1),

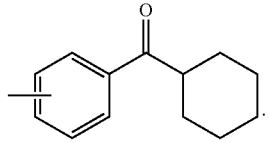
(j-1)

When $R_4$ is hydrogen, and R is 1-hydroxycyclohexyl, the photoinitiator residue represented by general formula (II) is a residue of phenyl-1-hydroxycyclohexyl ketone, which may be represented by the following general formula (j-2),

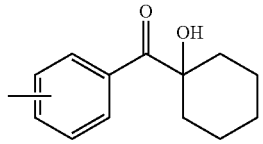
(j-2)

In an embodiment, the photoinitiator residue is represented by general formula (II), and R thereof is —$CR_1R_2R_3$, in which $R_1$ is selected from hydrogen or hydroxyl $R_2$ and $R_3$ are each independently selected from linear or branched $C_1$-$C_{20}$ alkyl, and $R_4$ in each instance is independently selected from hydrogen, and linear or branched $C_1$-$C_{20}$ alkyl.

In a further embodiment, the photoinitiator residue is represented by general formula (II), and R thereof is —$CR_1R_2R_3$, in which $R_1$ is hydroxyl, $R_2$ and $R_3$ are each independently selected from linear or branched $C_1$-$C_6$ alkyl (e.g., methyl), and $R_4$ is hydrogen. In addition, the divalent linkage represented by —Y-L- of general formula (I) is represented by general formula (IIIa), in which $R_6$ and $R_7$ are each independently selected from divalent linear or branched $C_1$-$C_6$ alkylene (e.g., ethylene).

The photoinitiator residue, in an embodiment, is represented by general formula (II), and R thereof is —$CR_1R_2R_3$, in which $R_1$ is hydroxyl, $R_2$ and $R_3$ are each methyl, and $R_4$ is hydrogen. In addition, the divalent linkage represented by —Y-L- of general formula (I) is represented by general formula (III), in which $R_6$ and $R_7$ are each ethylene. In this embodiment, Y of general formula (I) is S (sulfur), and the —Y-L-PI portion of the macro-photoinitiator represented by general formula (I), may be represented by the following general formula (k),

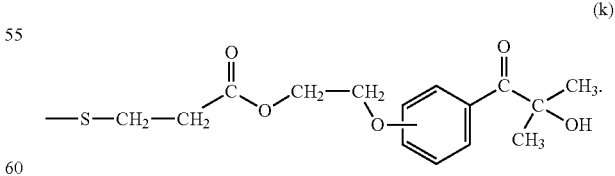
(k)

The macro-photoinitiator may be prepared by any suitable polymerization method. In an embodiment, the macro-photoinitiator is prepared by controlled radical polymerization. Controlled radical polymerization methods include, but are not limited to, atom transfer radical polymerization (ATRP), single electron transfer polymerization (SETP), reversible addition-fragmentation chain transfer (RAFT), and nitroxide-mediated polymerization (NMP).

When the macro-photoinitiator is prepared by controlled radical polymerization, such as ATRP or SETP, the initiator typically includes a transferable group (e.g., a radically transferable group), which may be a halo (halide or halogen) group. The halo (halide or halogen) group may be selected from fluoro, chloro, bromo, and/or iodo. Typically, the halo group is selected from chloro and/or bromo, and more typically bromo. The residue of the initiator, Φ of formula (I), is free of the transferable group. In addition, subscript-z of general formula (I) is from 1 to the average total number of radically transferable groups originally present on the initiator. For example, when the initiator is selected from di($C_1$-$C_6$-alkyl)-2,5-dihaloadipate, which has two radically transferable halo groups, z of formula (I) is 2.

Controlled radical polymerization, such as ATRP, is described generally as a "living polymerization," i.e., a chain-growth polymerization that propagates with essentially no chain transfer and essentially no chain termination. The molecular weight of a polymer prepared by controlled radical polymerization can be controlled by the stoichiometry of the reactants, i.e., the initial concentration of monomer(s) and initiator(s). In addition, controlled radical polymerization also provides polymers having characteristics including, for example, narrow molecular weight distributions, e.g., PDI values less than 2.5, and well defined polymer chain structure, e.g., block copolymers and alternating copolymers.

For purposes of illustrating controlled radical polymerization processes, the ATRP process will be described in further detail. The ATRP process may be described generally as comprising: polymerizing one or more radically polymerizable monomers in the presence of an initiation system; forming a polymer; and isolating the formed polymer. The initiation system typically includes: an initiator having a radically transferable atom or group; a transition metal compound, i.e., a catalyst, which participates in a reversible redox cycle with the initiator; and a ligand, which coordinates with the transition metal compound.

As discussed previously herein, initiators used in controlled radical polymerization methods, such as ATRP, typically, have at least one radically transferable group (e.g., a halo group), and the residue of the initiator (e.g., represented by Φ in formula (I) is free of the radically transferable group. The residue of the initiator may be selected from polymeric compounds. When the macro-photoinitiator is prepared by controlled radical polymerization, polymeric compounds (including oligomeric compounds) having one or more radically transferable groups may be used as initiators, and are herein referred to as "macroinitiators." Examples of macroinitiators include, but are not limited to, polystyrene prepared by cationic polymerization and having a terminal halide, e.g., chloride, and a polymer of 2-(2-bromopropionoxy) ethyl acrylate, and one or more alkyl(meth)acrylates, e.g., butyl acrylate, prepared by conventional non-living radical polymerization. Macroinitiators can be used in controlled radical processes, such as ATRP and SETP processes, to prepare graft polymers, such as, grafted block copolymers and comb copolymers.

In an embodiment of the present invention, the initiator is more particularly selected from halomethane, methylenedihalide, haloform, carbon tetrahalide, methanesulfonyl halide, p-toluenesulfonyl halide, methanesulfenyl halide, p-toluenesulfenyl halide, 1-phenylethyl halide, $C_1$-$C_6$-alkyl ester of 2-halo-$C_1$-$C_6$-carboxylic acid, p-halomethylstyrene, mono-hexakis(alpha-halo-$C_1$-$C_6$-alkyl)benzene, di($C_1$-$C_6$-alkyl)-2-halo-2-methyl malonate, $C_1$-$C_6$-alkyl 2-haloisobutyrate, di($C_1$-$C_6$-alkyl)-2,5-dihaloadipate, and mixtures thereof.

When the macro-photoinitiator is prepared by controlled radical polymerization, such as ATRP, the residue of the initiator, Φ of formula (I) is: typically free of the radically transferable group(s) of the initiator; and bonded to the macro-photoinitiator at (or through) the position where the radically transferable group was previously bonded. For purposes of non-limiting illustration, when the macro-photoinitiator is prepared by controlled radical polymerization, such as ATRP, and the initiator is diethyl-2-bromo-2-methyl malonate, the residue of the initiator Φ of formula (I), which is free of the transferable bromo group, may be represented by the following general formula (IVa),

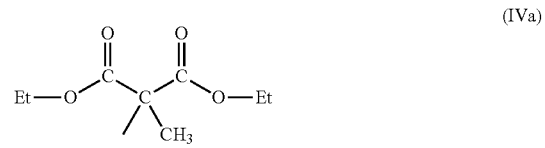

The diethyl-2-methyl malonate residue represented by formula (IVa) is bonded to the macro-photoinitiator at the 2-position thereof.

For purposes of further non-limiting illustration, when the macro-photoinitiator is prepared by controlled radical polymerization, such as ATRP, and the initiator is diethyl-2,5-dibromoadipate, the residue of the initiator Φ of formula (I), which is free of the transferable bromo groups, may be represented by the following general formula (IVb),

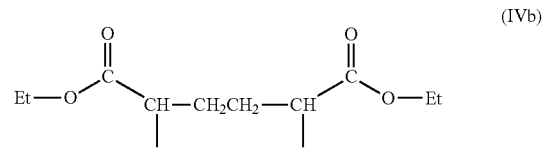

The diethyl-2,5-adipate residue represented by formula (IVb) is bonded to two separate polymer chain segments at the 2 and 5 positions thereof, and z of formula (I) correspondingly is 2.

Catalysts that may be used in the ATRP preparation of the macro-photoinitiator of the present invention, include any transition metal compound that can participate in a redox cycle with the initiator and the growing polymer chain. The transition metal compound is typically selected such that it does not form direct carbon-metal bonds with the polymer chain. Transition metal catalysts useful in preparing the ATRP preparation of the macro-photoinitiator of the present invention may be represented by the following general formula VI,

In formula (VI) TM is the transition metal, n is the formal charge on the transition metal having a value of from 0 to 7, and X is a counterion or covalently bonded component. Examples of suitable transition metals (TM) include, but are not limited to, Cu, Fe, Au, Ag, Hg, Pd, Pt, Co, Mn, Ru, Mo, Nb, and Zn. Examples of suitable counterions (X) include, but are not limited to, halogen, hydroxy, oxygen, $C_1$-$C_6$-alkoxy, cyano, cyanato, thiocyanato, and azido. In an embodiment, the transition metal is Cu(I) and counterion X is a halogen (e.g., chloride). The transition metal catalysts may be selected from copper halides, e.g., Cu(I)Cl. The transition metal catalyst may, in an embodiment, contain a small amount, e.g., 1 mole percent, of a redox conjugate, for example, Cu(II)$Cl_2$ when Cu(I)Cl is used.

Ligands that may be used in preparing macro-photoinitiator of the present invention by ATRP, include, but are not limited to, compounds having one or more nitrogen, oxygen, phosphorus, and/or sulfur atoms, which can coordinate to the transition metal catalyst compound, e.g., through sigma and/or pi bonds. Classes of useful ligands, include, but are not limited to, unsubstituted and substituted pyridines and bipyridines, porphyrins, cryptands, crown ethers (e.g., 18-crown-6), polyamines (e.g., ethylenediamine and N,N,N',N'',N''-pentamethyldiethylenetriamine PMDETA), glycols (e.g., alkylene glycols, such as ethylene glycol), carbon monoxide, and coordinating monomers (e.g., styrene, acrylonitrile and hydroxyalkyl(meth)acrylates). A class of ligands that may be used in the ATRP preparation of the macro-photoinitiator include the substituted bipyridines (e.g., 4,4'-dialkyl-bipyridyls).

In preparing the macro-photoinitiator of the present invention by ATRP, the amounts and relative proportions of initiator, transition metal compound, and ligand are those for which ATRP is most effectively performed. The amount of initiator used can vary widely and is typically present in the reaction medium in a concentration of from $10^{-4}$ moles/liter (M) to 3 M, for example, from $10^{-3}$ M to $10^{-1}$ M. As the molecular weight of the macro-photoinitiator can be directly related to the relative concentrations of initiator and monomer(s), the molar ratio of initiator to monomer is an important factor in polymer preparation. The molar ratio of initiator to monomer is typically within the range of $10^{-4}$:1 to 0.5:1, for example, $10^{-3}$:1 to $5 \times 10^{-2}$:1.

In preparing the macro-photoinitiator of the present invention by ATRP, the molar ratio of transition metal compound to initiator is typically in the range of 100:1 to 10:1, for example, 0.1:1 to 5:1. The molar ratio of ligand to transition metal compound is typically within the range of 0.001:1 to 100:1, for example, 0.2:1 to 10:1.

The macro-photoinitiator of the present invention may be prepared in the absence of solvent, i.e., by means of a bulk polymerization process. Generally, the macro-photoinitiator is prepared in the presence of a solvent, typically water and/or an organic solvent. Classes of useful organic solvents include, but are not limited to, esters of carboxylic acids, ethers, cyclic ethers, $C_5$-$C_{10}$ alkanes, $C_5$-$C_8$ cycloalkanes, aromatic hydrocarbon solvents, halogenated hydrocarbon solvents, amides, nitriles, sulfoxides, sulfones, ketones and mixtures thereof. Supercritical solvents, such as $CO_2$, $C_1$-$C_4$ alkanes and fluorocarbons, may also be employed. A more typical class of solvents are the aromatic hydrocarbon solvents, for example, xylene, and mixed aromatic solvents such as those commercially available from Exxon Chemical America under the trademark SOLVESSO.

The macro-photoinitiator, when prepared by ATRP, is typically prepared at a reaction temperature within the range of 25° C. to 140° C. (e.g., from 50° C. to 100° C.) and a pressure within the range of 1 to 100 atmospheres, usually at ambient pressure. The atom transfer radical polymerization is typically completed in less than 24 hours (e.g., between 1 and 8 hours).

When the macro-photoinitiator is prepared in the presence of a solvent, the solvent may optionally be removed after the polymer has been formed, by appropriate means as are known to those of ordinary skill in the art (e.g., vacuum distillation). Alternatively, the polymer may be precipitated out of the solvent, filtered, washed, and dried according to known methods. After removal of, or separation from, the solvent, the macro-photoinitiator (or polymer precursor thereof) typically has a solids (as measured by placing a 1 gram sample in a 110° C., or higher, oven for 60 minutes) of at least 95 percent, and typically at least 98 percent, by weight based on total polymer weight.

Prior to use in the curable compositions of the present invention, the ATRP transition metal catalyst and its associated ligand are typically separated or removed from the macro-photoinitiator. Removal of the ATRP catalyst is achieved using known methods, including, for example, adding a catalyst binding agent to the a mixture of the polymer, solvent and catalyst, followed by filtering. Examples of suitable catalyst binding agents include, but are not limited to, alumina, silica, clay, or a combination thereof. A mixture of the polymer, solvent, and ATRP catalyst may be passed through a bed of catalyst binding agent. Alternatively, the ATRP catalyst may be oxidized in situ and retained in (or with) the macro-photoinitiator.

The macro-photoinitiator may have gross polymer architecture selected from linear polymer architecture, branched polymer architecture, hyperbranched polymer architecture, star polymer architecture, graft polymer architecture, and combinations or mixtures thereof. The term gross polymer architecture (or gross architecture) refers to the 3 dimensional structure of the macro-photoinitiator or portions thereof. Typically, the macro-photoinitiator has substantially linear polymer architecture. The form, or gross architecture, of the polymer can be controlled by the choice of initiator and monomers used in its preparation. Linear macro-photoinitiators may be prepared (e.g., via ATRP) by using initiators having one or two radically transferable groups, e.g., diethyl-2-halo-2-methyl malonate and $\alpha,\alpha'$-dichloroxylene. Branched macro-photoinitiators may be prepared by using branching monomers, i.e., monomers containing radically transferable groups or more than one ethylenically unsaturated radically polymerizable group, such as 2-(2-bromopropionoxy)ethyl acrylate, p-chloromethylstyrene, and diethyleneglycol bis(methacrylate). Hyperbranched macro-photoinitiators may be prepared by increasing the amount of branching monomer used.

Marco-photoinitiators having star polymer architecture may be prepared using initiators having three or more radically transferable groups (e.g., hexakis(bromomethyl)benzene). As is known to the skilled artisan, star polymers may be prepared by core-arm or arm-core methods. In the core-arm method, the star polymer is prepared by polymerizing monomers in the presence of the polyfunctional initiator (e.g., hexakis(bromomethyl)benzene). Polymer chains, or arms, of similar composition and architecture grow out from the initiator core, in the core-arm method.

In the arm-core method, the arms are prepared separately from the core and optionally may have different compositions, architecture, molecular weight, and PDI's. The arms may, for example, have different photoinitiator residues. After the preparation of the arms, they are attached to the core. For example, the arms may be prepared by ATRP using glycidyl functional initiators. These arms can then be attached to a core having three or more active hydrogen groups that are reactive with epoxides (e.g., carboxylic acid or hydroxyl groups). The core can be a molecule, such as citric acid, or a core-arm star polymer prepared by ATRP and having terminal reactive hydrogen containing groups (e.g., carboxylic acid, thiol, or hydroxyl groups). The reactive hydrogen groups of the core may react with the residue of the glycidyl functional initiator.

An example of a core prepared by ATRP methods that can be used as a core in an ATRP arm-core star polymer is described as follows. In the first stage, 6 moles of methyl methacrylate are polymerized in the presence of one mole of 1,3,5-tris(bromomethyl)benzene. In the second stage, 3 moles of 2-hydroxyethyl methacrylate are fed to the reaction mixture. Three living ATRP prepared arms of varying or equivalent composition, and each containing a single epoxide group (e.g., the residue of an epoxide functional initiator) may be connected to the hydroxy terminated core by reaction between the hydroxy groups of the core and the epoxide group in each of the arms. After attachment of the arms to the core, ATRP polymerization of the so-attached arms may optionally be further continued.

Macro-photoinitiators in the form of graft polymers may be prepared using a macroinitiator, as previously described herein. Typically, the macroinitiator used to form a graft polymer, by ATRP, has a plurality of pendent radically transferable groups. Macro-photoinitiators in the form of graft polymers may be further described as having comb-like gross polymer architecture.

The macro-photoinitiator may have backbone architecture (i.e., the arrangement of monomer residues or units along the polymer backbone) selected from homopolymer backbone architecture, random copolymer backbone architecture, block copolymer backbone architecture, and gradient copolymer backbone architecture. These various backbone architectures have been discussed and described previously herein with regard to the $-(M)_p$-portion of general formula (I).

When prepared by controlled radical polymerization, such as ATRP or SETP, the macro-photoinitiator may be prepared in two steps. In the first step, the controlled radical polymerization is performed and results in the formation of an intermediate polymer represented by the following general formula (VII), $$\Phi\text{-}[[\text{-}(M)_p\text{-}]_x\text{-}T]_z \qquad \text{(VII)}$$

In formula (VII), the symbols, $\Phi$, M, p, x, and z have the same meanings as described previously herein with regard to formula (I). The symbol T in formula (VII) represents a residue of the radically transferable group of the initiator, which is typically a halo group (e.g., bromo). The intermediate polymer represented by formula (VII) is then reacted with a thiol functional photoinitiator represented by the following general formula (VIII), $$\text{HY-L-PI} \qquad \text{(VIII)}$$

In formula (VIII)-YH represents a thiol group (—SH) or a hydroxyl group (—OH), and L and PI have the same meanings as described previously herein, for example, with regard to formula (I).

The reaction between the polymer intermediate represented by formula (VII) and the thiol functional or hydroxyl functional (e.g., phenol functional) photoinitiator represented by formula (VIII) may be conducted in accordance with art-recognized $S_N2$ methods. In the reaction therebetween, and when Y is S, the terminal halo group (T) of the intermediate polymer represented by formula (VII) is substituted with the thiol group of the thiol functional photoinitiator represented by formula (VIII), resulting in the formation of a sulfide linkage and correspondingly the macro-photoinitiator of the present invention represented by formula (I), in which Y is S. Alternatively, when Y is O, the terminal halo group (T) of the intermediate polymer represented by formula (VII) is substituted with the hydroxyl group of the hydroxyl functional photoinitiator represented by formula (VIII), resulting in the formation of an ether linkage and correspondingly the macro-photoinitiator of the present invention represented by formula (I), in which Y is O. In an embodiment, when Y of formula (VIII) is O, the hydroxyl group (—OH) thereof is bonded to an aromatic group (e.g., L, or directly to PI when L is a bond), such as a phenyl group (in which case the hydroxyl group of formula (VIII) may be referred to as an aromatic hydroxyl group, such as a phenol group).

The intermediate polymer represented by formula (VII) may be worked-up to remove, for example, initiator components (e.g., copper catalyst) and/or co-products resulting from the controlled radical polymerization process. Alternatively, removal of initiator components and/or co-products resulting from the controlled radical polymerization process may be conducted after the subsequent substitution reaction (e.g., $S_N2$ reaction) that results in formation of the macro-photoinitiator of the present invention, for example as represented by formula (I).

Preparation of macro-photoinitiators according to the present invention that are terminated with a residue of a thiol functional photoinitiator (e.g., in which Y of formulas (I) and (VIII) is S) is described in further detail in the examples. Macro-photoinitiators according to the present invention that are terminated with a residue of a hydroxyl functional photoinitiator (e.g., in which Y of formulas (I) and (VIII) is O) may be prepared in accordance with art-recognized methods. For purposes of non-limiting illustration, the preparation of a macro-photoinitiator according to the present invention that is terminated with a residue of a hydroxyl functional photoinitiator may be generally described as follows with reference to the following Synthetic Scheme-A.

Synthetic Scheme-A

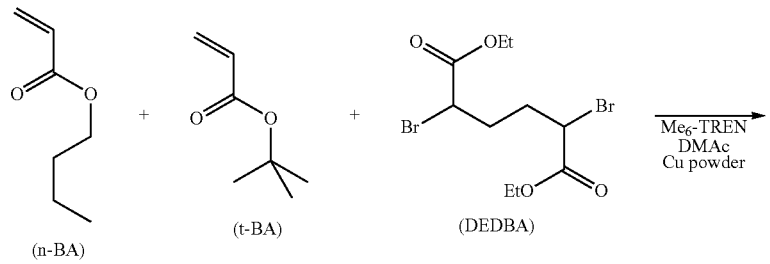

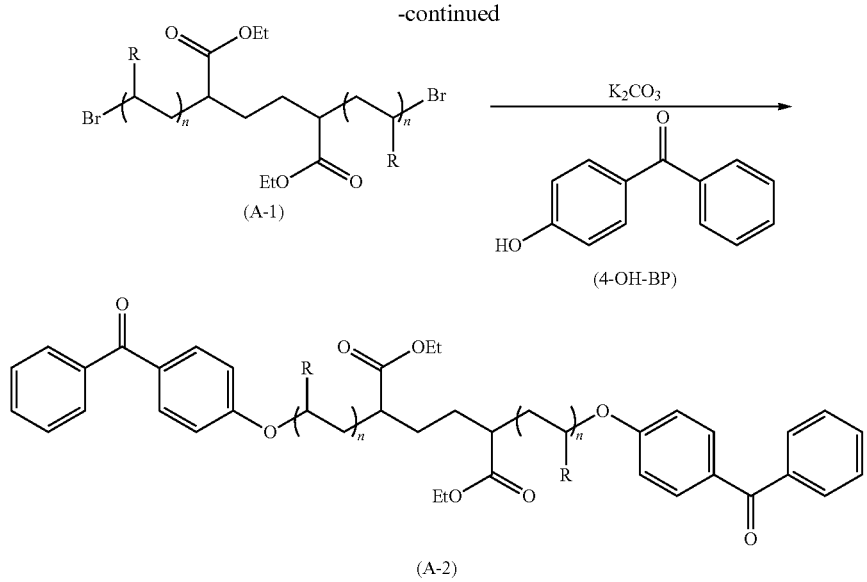

(A-2)

R = —C(O)O(CH$_2$)$_3$CH$_3$ (95%) + —C(O)OC(CH$_3$)$_3$ (5%)
Me$_6$-TREN = tris[2-(dimethylamino)ethyl]amine
DMAc = dimethylacetamide In a first stage, a bromo-terminated polyacrylate intermediate (A-1) may be prepared using a single electron transfer polymerization method. For example, a blend of n-butyl acrylate (n-BA) and t-butyl acrylate (t-BA) having a mole ratio of 20 to 1 (e.g., 128 g; 1.0 moles of total acrylate), tris[2-(dimethylamino)ethyl]amine (Me$_6$-TREN) (e.g., 0.037 g; 0.161 millimoles), copper powder (e.g., 0.20 g; <10 µm particle size) and diethyl meso-2,5-dibromadipate (DEDBA) (e.g., 1.16 g; 3.23 millimoles) is polymerized to 100% conversion of acrylate monomers in dimethylacetamide (DMAc), with continuous stirring and under a nitrogen sweep in a suitable reaction vessel (e.g., a round bottom glass flask). A ratio of acrylate monomers to solvent of 1 to 2 may be used. The bromo-terminated polyacrylate intermediate (A-1) may have any suitable molecular weight, such as a number average molecular weight of about 40,000, as would be determined in accordance with art-recognized methods (e.g., as described in further detail in Example-2 herein). The bromo-terminated polyacrylate intermediate (A-1) may be worked-up in accordance with art-recognized methods (e.g., by passing the polymer solution through a bed of neutral alumina to remove copper powder and dissolved copper salts).

In a second stage, the bromo-terminated polyacrylate intermediate (A-1) may be converted to the macro-photoinitiator (A-2) by substituting the terminal bromo groups with a hydroxyl functional photoinitiator, such as 4-hydroxybenzophenone (4-OH-BP). For example, under non-actinic light, such as yellow light, potassium carbonate (e.g., 1.173 g; 8.50 millimoles) and 4-hydroxybenzophenone (e.g., 1.40 g; 7.10 millimoles) may be added to the polymer solution containing the bromo-terminated polyacrylate intermediate (A-1), and the mixture heated and held at 50° C. for 6 hours. The resulting solution is typically filtered and the solvent removed under reduced pressure to provide the macro-photoinitiator (A-2) according to the present invention, which may be described generally as a di-benzophenone-terminated poly (n-butyl acrylate-co-t-butyl acrylate).

The present invention also relates to curable compositions that include: (a) at least one macro-photoinitiator as described previously herein with reference to formula (I); and (b) at least one reactant having at least one ethylenically unsaturated radically polymerizable group, such as, one or more $C_1$-$C_{20}$ alkyl(meth)acrylates. The curable composition of the present invention is cured by exposure to actinic radiation. As such, the curable compositions of the present invention may be referred to as photocurable compositions.

The reactant may include a monomer selected from vinyl monomers, allylic monomers, olefins, and combinations thereof, in each case having at least at least one (e.g., 1, 2, or more) ethylenically, unsaturated radically polymerizable group. The vinyl monomers, allylic monomers, and olefins of the reactant may be selected from those classes and examples of monomers as described previously herein with regard to the monomers from which the macro-photoinitiator is prepared.

In an embodiment, the reactant of the curable composition includes monomers having at least two ethylenically unsaturated radically polymerizable groups, for example 2, 3, or 4 ethylenically unsaturated radically polymerizable groups. Monomers having at least two ethylenically unsaturated radically polymerizable groups may be selected from art-recognized classes and examples thereof. In an embodiment, monomers of the curable composition, having at least two ethylenically unsaturated radically polymerizable groups (e.g., polyfunctional monomers) are selected from (meth) acrylate functional polyols. The polyols may be monomeric (e.g., alkylene glycols, such as $C_2$-$C_6$ alkylene glycols), oligomeric (e.g., di, tri, or tetra alkylene glycols), or polymeric (e.g., hydroxyl functional polyethers, such as polyethylene ether, and polytetrahydrofuran). For example, the polyfunctional monomer may be selected from: ethylene glycol di(meth)acrylate; propylene glycol di(meth)acrylate; diethylene glycol di(meth)acrylate; dipropylene glycol di(meth) acrylate; triethylene glycol di(meth)acrylate; tripropylene glycol di(meth)acrylate; tetraethylene glycol di(meth)acrylate; tetrapropylene glycol di(meth)acrylate; trimethylolpropane tri(meth)acrylate; and pentaerythritol tetra(meth)acrylate.

In an embodiment, the monomer of the reactant includes, in addition or alternatively to a polyfunctional monomer, at least one of alkyl(meth)acrylates having from 1 to 20 carbon atoms in the alkyl group, vinyl aromatic monomers, vinyl halides, vinyl esters of carboxylic acids, olefins, acrylonitrile, methacrylonitrile, N,N-di($C_1$-$C_6$ alkyl)-(meth)acrylamide and combinations, and/or mixtures of two or more thereof, which are in each case as described previously herein with regard to the monomers from which the macro-photoinitiator is prepared.

In a further embodiment of the present invention, the curable composition is a curable thiol-ene composition. Curable thiol-ene compositions according to the present invention typically include: (a) at least one macro-photoinitiator as described previously herein with reference to formula (I); (b) at least one reactant having at least one ethylenically unsaturated group that is radically polymerizable, which may be selected from those classes and examples of monomers as described previously herein; and (c) a thiol functional material having at least one thiol group. While not intending to be bound by any theory, and based on evidence at hand, thiol-ene compositions are believed to polymerize (or cure) by way of a free-radical step-growth mechanism, rather than a chain-growth mechanism. Thiol-ene compositions according to the present invention may have desirable optical properties, such as optical clarity and increased refractive indices, and as such may be used as adhesives in the assembly of optical components (e.g., ophthalmic and non-ophthalmic lenses, including photochromic lenses). The macro-photoinitiator may be present in the thiol-ene composition in any suitable amount, for example, from 5 to 80 percent by weight, based on the total weight of the thiol-ene composition.

With the thiol-ene compositions of the present invention, the ethylenically unsaturated reactant (b) typically has at least two (e.g., 2, 3, 4, 5 or 6) ethylenically unsaturated groups, and undergoes minimal or substantially no self-polymerization (e.g., substantially no radical polymerization as between the ethylenically unsaturated groups). The thiol functional material (c) typically has at least two (e.g., 2, 3, 4, 5 or 6) thiol groups. In an embodiment, the molar ratio of ethylenically unsaturated groups of ethylenically unsaturated reactant (b) and thiol groups of thiol functional material (c) is typically substantially equivalent (e.g., substantially 1 to 1). The ethylenically unsaturated reactant (b) and the thiol functional material (c) may be present in the thiol-ene compositions of the present invention in any suitable amount. In an embodiment, the ethylenically unsaturated reactant (b) and the thiol functional material (c) are present in the thiol-ene compositions of the present invention in a combined amount of from 20 to 95 percent by weight, based on the total weight of the thiol-ene composition.

The ethylenically unsaturated reactant (b) of the thiol-ene compositions of the present invention may have ethylenically unsaturated groups selected from those as discussed previously herein, for example: alkenes (or olefins), such as divinyl benzene; cyclic olefins (e.g., cyclooctene); ethylenically unsaturated ethers (e.g., vinyl ethers and/or propenyl ethers); allyl groups; alkynes (or acetylenes); polycyclic olefins (e.g., norbornenes); and combinations thereof. In an embodiment, the ethylenically unsaturated reactant (b) of the thiol-ene composition includes triallyl trazine trione. In addition to including ethylenically unsaturated reactants that undergo minimal or substantially no self-polymerization, reactant (b), of the thiol-ene composition, may optionally further include ethylenically unsaturated reactants that do undergo self-polymerization, such as, for example, (meth)acrylate functional materials, as described previously herein.

Examples of polyfunctional olefin monomers from which ethylenically unsaturated reactant (b) of the thiol-ene composition may be selected include, but are not limited to: divinyl benzene, e.g., 1,2-divinyl benzene, 1,3-divinyl benzene, 1,4-divinyl benzene and mixtures of structural isomers of divinyl benzene; diisopropenyl benzene, e.g., 1,2-diisopropenyl benzene, 1,3-diisopropenyl benzene, 1,4-diisopropenyl benzene and mixtures of structural isomers of diisopropenyl benzene; trivinyl benzene, e.g., 1,2,4-triethenyl benzene, 1,3,5-triethenyl benzene and mixtures of structural isomers of trivinyl benzene; divinyl naphthalene, e.g., 2,6-diethenyl naphthalene, 1,7-diethenyl naphthalene, 1,4-diethenyl naphthalene and mixtures of structural isomers of divinyl naphthalene; halogen substituted derivatives of divinyl benzene, diisopropenyl benzene, trivinyl benzene and divinyl naphthalene, e.g., 2-chloro-1,4-diethenyl benzene; and mixtures of such aromatic monomers.

The thiol functional material (c) of the thiol-ene compositions may be selected from known thiol functional materials, such as, mercaptoacetates, polydisulfides, mercaptanized olefins and mercaptanized epoxides. Examples of thiol functional materials that may be included in the thiol-ene compositions of the present invention include, but are not limited to, 2,2'-thiodiethanethiol, pentaerythritol tetrakis(3-mercaptopropionate), pentaerythritol tetrakis(2-mercaptoacetate), trimethylolpropane tris(3-mercaptopropionate), trimethylolpropane tris(2-mercaptoacetate), 4-mercaptomethyl-3,6-dithia-1,8-octanedithiol, 4-tert-butyl-1,2-benzenedithiol, 4,4'-thiodibenzenethiol, benzenedithiol, ethylene glycol di(2-mercaptoacetate), ethylene glycol di(3-mercaptopropionate), polyethylene glycol di(2-mercaptoacetate), polyethylene glycol di(3-mercaptopropionate) and mixtures of such polythiol monomers.

In an embodiment, and for purposes of non-limiting illustration, a thiol-ene composition according to the present invention includes: at least one macro-photoinitiator as described previously herein with reference to formula (I); ethylenically unsaturated reactant (b) that includes triallyl triazine trione; and thiol functional material (c) that includes pentaerythritol tetramercaptopropionate.

The curable compositions of the present invention may be prepared by art-recognized methods. For example, the macro-photoinitiator, reactant, and any optional components, such as additives and solvents, are mixed together in any order in a suitable container (e.g., a stainless steel container) by suitable mixing means, such as an impeller. To avoid overheating the curable composition (which may lead to premature polymerization), the container may be fitted with a heat-exchanging jacket through which a cooled liquid is controllably passed.

The relative amounts of components (e.g., macro-photoinitiator and reactant) of the curable composition of the present invention may be selected so as to provide a cured product therefrom having desirable physical properties, such as hardness, flexibility, and toughness. Typically, the weight ratio of macro-photoinitiator (a) to reactant (b), in the absence of thiol functional material (c), is from 9:1 to 1:9, for example, from 7:1 to 1:7 or from 5:1 to 1:5 (e.g., 2.5:1 or 2.3:1).

In addition to the macro-photoinitiator, reactant and optional thiol functional material, the curable composition of the present invention may optionally include further components, such as photoinitiators (that are other than the macro-photoinitiator of the present invention, i.e., additional photoinitiators), stabilizers, solvents, flow modifiers, and toughening agents.

Additional photoinitiators that may be included in the curable compositions of the present invention include, but are not limited to, photoinitiators available commercially from Ciba-Geigy Corp., Tarrytown, N.Y. under the tradenames "IRGA- CURE" and "DAROCUR." Examples of such additional photoinitiators include, but are not limited to, "IRGACURE" 184 (1-hydroxycyclohexyl phenyl ketone), 907 (2-methyl-1-[4-(methylthio)phenyl]-2-morpholino propan-1-one), 369 (2-benzyl-2-N,N-dimethylamino-1-(4-morpholinophenyl)-1-butanone), 500 (the combination of 1-hydroxy cyclohexyl phenyl ketone and benzophenone), 651 (2,2-dimethoxy-2-phenyl acetophenone), 1700 (the combination of bis(2,6-dimethoxybenzoyl-2,4-,4-trimethyl pentyl) phosphine oxide and 2-hydroxy-2-methyl-1-phenyl-propan-1-one), and 819 [bis(2,4,6-trimethyl benzoyl)phenyl phosphine oxide]. Further examples of additional photoinitiators include, but are not limited to, "DAROCUR" 1173 (2-hydroxy-2-methyl-1-phenyl-1-propane) and 4265 (the combination of 2,4,6-trimethylbenzoyldiphenyl-phosphine oxide and 2-hydroxy-2-methyl-1-phenyl-propan-1-one). Additional photoinitiators that are activated by exposure to visible light (e.g., blue light) may also be used, such as, dl-camphorquinone and "IRGACURE" 784DC. Combinations of two or more such additional photoinitiators may also be used in the curable compositions of the present invention.

Further classes of additional photoinitiators include, alkyl pyruvates, such as methyl, ethyl, propyl, and butyl pyruvates, and aryl pyruvates, such as phenyl, benzyl, and appropriately substituted derivatives thereof.

Examples of additional photoinitiators that are, in particular, activated by exposure to ultraviolet light and/or visible light, include, but are not limited to, 2,2-dimethoxy-2-phenyl acetophenone (e.g., "IRGACURE" 651), and 2-hydroxy-2-methyl-1-phenyl-1-propane (e.g., "DAROCUR" 1173), bis (2,4,6-trimethyl benzoyl)phenyl phosphine oxide (e.g., "IRGACURE" 819), and the ultraviolet/visible photoinitiator combination of bis(2,6-dimethoxybenzoyl-2,4-,4-trimethyl-pentyl) phosphine oxide and 2-hydroxy-2-methyl-1-phenyl-propan-1-one (e.g., "IRGACURE" 1700), as well as, the visible photoinitiator bis(m,5,2,4-cyclopentadien-1-yl)-bis[2,6-difluoro-3-(1H-pyrrol-1-yl)phenyl]titanium (e.g., "IRGACURE" 784DC).

The curable compositions of the present invention may be formulated in accordance with art-recognized methods to have desirable flow properties, such as low viscosity, medium viscosity, high viscosity, or thixotropic flow properties. Examples of flow modifiers that may be added to the curable compositions of the present invention include, but are not limited to, polymethyl(meth)acrylates and fumed silicas. For example, in applications where it is desirable for the curable composition to be wicked into a small gap (e.g., of 2.5 microns or less) between substrates that are to be bonded together, a low viscosity is typically desirable. When free of art-recognized thickeners and/or viscosity modifiers, the curable compositions of the present invention typically have a low viscosity (e.g., from 1 to 500 mPa·s at 25° C.).

Medium viscosity formulations (e.g., from 500 to 5000 mPa·s at 25° C.) may be more appropriate in applications where greater flow control is desirable, such as bonding together molded polymeric parts. High viscosity formulations (e.g., from 5000 to 5,000,000 mPa·s at 25° C.) may be more appropriate in applications involving porous substrates and/or substrates with larger gaps (e.g., greater than about 12 microns).

The curable compositions of the present invention may be rendered thixotropic (e.g., in the form of a thixotropic paste) through addition of powdered organic fillers having a particle size of about 2 to 200 microns as is taught by U.S. Pat. No. 4,105,715 (Gleave) or thickened by a copolymer or terpolymer resin to improve peel strength as is taught by U.S. Pat. No. 4,102,945 (Gleave), the disclosures of each of which are hereby incorporated herein by reference.

The resistance of the curable compositions of the present invention to thermal degradation at elevated temperatures may be enhanced by the inclusion of antioxidants, such as phenolic compounds.

Art recognized elastomeric rubber materials may be included in the curable compositions of the present invention for purposes of improving the toughness of cured products prepared therefrom, as is known to a skilled artisan. Art recognized anhydrides may be included in the curable compositions of the present invention for purposes of improving the hot strength of cured products prepared therefrom, as is known to a skilled artisan.

The present invention also relates to a method of curing a curable composition, which includes: (a) providing an amount of the curable composition (e.g., on a substrate); and (b) subjecting or exposing the curable composition to actinic radiation, thereby effecting cure thereof.

The curable composition of the present invention may be a curable adhesive composition. When used as an adhesive, the amount of curable composition provided should be sufficient to cure and form an adequate bond to the substrate surfaces between which it is applied. For example, application of the curable composition may be achieved by dispensing the composition in drop-wise fashion, or as a liquid stream, brush-applied, dipping, and the like, to form a thin film. Application of the curable composition may depend on the flowability or viscosity of the composition. To that end, viscosity modifiers, as described above, may be included in the composition. The curable composition may be applied to certain portions of the substrate surface, or over the entire surface of the substrate to be bonded, depending on the particular application.

The curable composition of the present invention may be a curable molding composition. When used to form a molded article, such as a shaped molded article, the curable composition is typically introduced (e.g., injected) into a mold. The mold is typically adapted to allow for the exposure of the curable composition residing therein to actinic radiation. For example, the mold may be fitted with a window that is transparent to actinic radiation. The curable composition is exposed to actinic radiation while in the mold, and allowed to cure. The mold is typically opened and the molded article (e.g., a gasket or lens, such as an optical lens) is removed therefrom.

The actinic radiation, used to cure the curable compositions of the present invention, may be selected from, for example, ultraviolet light, visible light, electron beam, x-rays, infrared radiation, and combinations thereof. Typically, the actinic radiation is ultraviolet light. Sources of ultraviolet light include, for example, "H", "D", "V", "tX", "M", and "A" lamps, mercury arc lamps, and xenon arc lamps (e.g., including those commercially available from Loctite Corporation, Rocky Hill, Conn., Fusion UV Curing Systems, Buffalo Grove, Ill., or Spectroline, Westbury, N.Y.). Additional useful sources of ultraviolet light include: microwave-generated ultraviolet radiation; solar light sources; and fluorescent light sources. Reflectors and/or filters may be used in conjunction with the actinic radiation, for purposes of focusing the emitted radiation onto or into the curable composition, or selecting a particular region of the electromagnetic spectrum. Similarly, the actinic radiation may be generated directly in a steady fashion or in an intermittent fashion, so as to minimize the degree of heat build-up.

The intensity of actinic radiation, number of exposures, and length (or time) of exposures to the actinic radiation may be selected individually or in any combination so as to achieve a desirable degree of cure, which is typically complete cure of the curable composition. With regard to adjusting the intensity of the actinic radiation, the lamp employed should have a power rating of at least about 100 watts per inch (at least about 40 watts per cm), with a power rating of at least about 300 watts per inch (at least about 120 watts per cm) being particularly desirable. Also, since the macro-photoinitiator of the present invention may be designed so as to shift the wavelength within the electromagnetic radiation spectrum at which cure occurs, it may be desirable to use a source of electromagnetic radiation having properties or variables (e.g., wavelength, distance, and the like) that are readily and controllably adjustable.

During the curing process, the curable composition is exposed to a source of actinic radiation that emits an amount of energy (e.g., measured in units of $KJ/m^2$) determined by parameters including: the size, type, and geometry of the source; the duration of the exposure to electromagnetic radiation; the intensity of the radiation (and that portion of radiation emitted within the region appropriate to effect curing); the absorbency of electromagnetic radiation by any intervening materials, such as substrates; and the distance the curable composition lies from the source of actinic radiation.

To effect cure, the source of actinic radiation may remain stationary while the curable composition passes through its path. Alternatively, a substrate coated with the curable composition may remain stationary while the source of actinic radiation passes thereover or therearound to complete the transformation from curable composition to reaction product. Further alternatively, both may traverse one another, or both may remain stationary, provided that the curable composition is exposed to actinic radiation sufficient to effect cure.

Examples of commercially available curing systems that may be used to cure the curable compositions of the present invention include, but are not limited to: the "ZETA" 7200 or 7400 ultraviolet curing chamber (Loctite Corporation, Rocky Hill, Conn.); Fusion UV Curing Systems F-300 B (Fusion UV Curing Systems, Buffalo Grove, Ill.); Hanovia UV Curing System (Hanovia Corp., Newark, N.J.); BlackLight Model B-100 (Spectroline, Westbury, N.Y.); and RC500 A Pulsed UV Curing System (Xenon Corp., Woburn, Mass.). A Sunlighter UV chamber fitted with low intensity mercury vapor lamps and a turntable may be employed to cure the curable compositions of the present invention.

When used to form a film, such as an adhesive film, or coating, the curable composition of the present invention is typically applied to the surface of a substrate. Substrates to which the curable composition may be applied are numerous. Substrates to which the curable compositions of the present invention may be applied, may include organic materials (e.g., organic polymers), inorganic materials (e.g., ceramics and/or silica glass), metals (e.g., steel, such as cold rolled steel), and combinations thereof. If the curable composition is interposed between two substrates, at least one of the substrates is typically transparent to the actinic radiation used to effect cure thereof. Examples of organic polymer materials include acrylics, epoxies, polyolefins, polycarbonates, polysulfones (e.g., polyether sulfone), polyvinyl acetates, polyamides, polyetherimides, polyimides and derivatives, and co-polymers thereof with which may be blended or compounded art-recognized additives for aiding processability or modifying the physical properties and characteristics of the material to be used as a substrate. Examples of co-polymers, which may be employed as substrates include acrylonitrile-butadiene-styrene, styrene-acrylonitrile cellulose, aromatic copolyesters based on terephthallic acid, p,p-dihydroxybiphenyl and p-hydroxy benzoic acid, polyalkylene (such as polybutylene or polyethylene) terephthalate, polymethyl pentene, polyphenylene oxide or sulfide, polystyrene, polyurethane, polyvinylchloride, and the like. Organic polymers, including organic co-polymers, that are capable of transmitting actinic radiation, are often used.

For purposes of non-limiting illustration, a substrate having the curable composition applied thereon, may be positioned within an actinic radiation curing apparatus, such as the "ZETA" 7200 ultraviolet curing chamber, equipped with an appropriate source of actinic radiation, such as ultraviolet radiation, at an appropriate distance therefrom, such as within the range of about 1 to 2 inches (2.5 to 5 cm), with about 3 inches (7.6 cm) being desirable. As noted above, the composition-coated substrate may remain in position or may be passed thereunder at an appropriate rate, such as within the range of about 1 to about 60 seconds per foot (0.03 to about 2 seconds per cm), for example, about 5 seconds per foot (about 0.16 seconds per cm). Such passage may occur one or more times, or as needed to effect cure of the composition on the substrate. The length of exposure may be in the range of a few seconds or less (for one time exposure) to tens of seconds or longer (for either a one-time exposure or a multiple-pass exposure) if desired, depending on the depth of the composition to be cured and, of course, on the components of the composition themselves.

The curable compositions of the present invention may be used to prepare cured products in the form of films that are formed separate from a substrate (e.g., stand-alone films), and which may be later applied to, adhered to, or positioned on a substrate in a subsequent step. The film so formed from the curable composition of the present invention may be self-adhering to the substrate to which it is later applied, and as such, not requiring the use of separate adhesive agents. Art-recognized film fabricating methods may be employed to prepare films (e.g., stand-alone films) from the curable compositions of the present invention, such as calendaring, casting, rolling, coating, extrusion, and thermoforming. With regard to coating, conventional techniques, such as curtain coating, spray coating, dip coating, spin coating, roller coating, brush coating, or transfer coating may be used.

The present invention is more particularly described in the following examples, which are intended to be illustrative only, since numerous modifications and variations therein will be apparent to those skilled in the art. Unless otherwise specified, all parts and percentages are by weight.

EXAMPLES

Example-1

A thiol-functional photoinitiator, 1-[4-(2-{2'-mercaptopropionate}ethoxy)-phenyl]-2-hydroxy-2-methyl-1-propane-1-one (C), used in the synthesis of macro-photoinitiators according to the present invention was prepared in accordance with the following description by means of an esterification reaction between 2-mercapopropionic acid (A) and 1-[4-(2-hydroxyethoxy)-phenyl]-2-hydroxy-2-methyl-1-propane-1-one (B). The synthesis of the thiol-functional photoinitiator (C) is summarized in the following Synthetic Scheme-1.

Synthetic Scheme-1

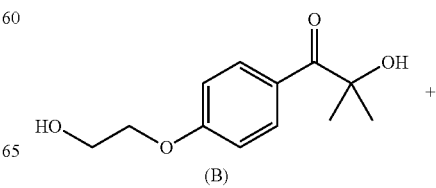

(B)

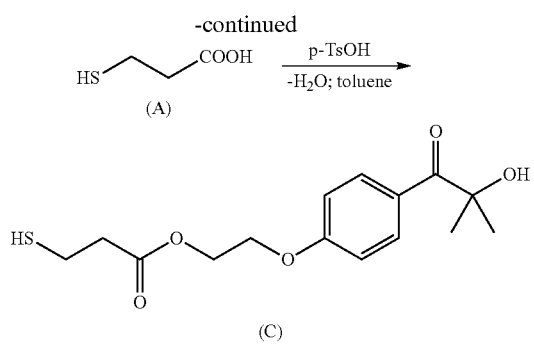

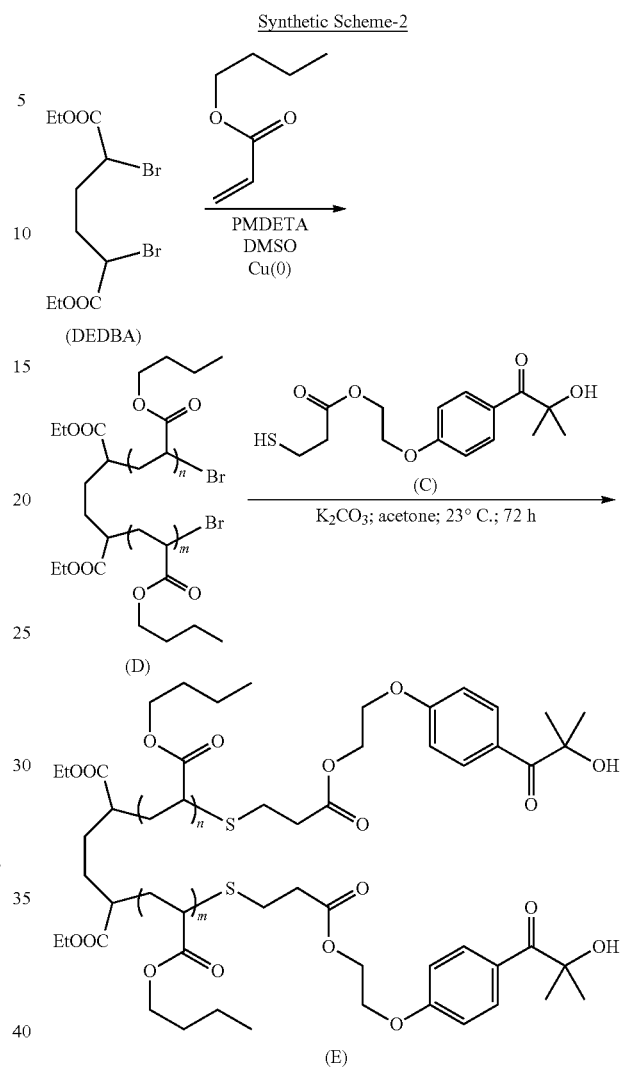

The synthesis was conducted under yellow lighting. To a 1-L reaction flask fitted with a Dean Stark separator, reflux condenser, thermocouple, magnetic stirrer, and heating mantel was added 1-[4-(2-hydroxyethoxy)-phenyl]-2-hydroxy-2-methyl-1-propane-1-one (B) (67.247 g; 0.30 moles), 2-mercaptopropionic acid (A) (31.822 g; 0.30 moles), toluene (200 mL), and p-toluenesulfonic acid (pTsOH) (0.901 g). The mixture was stirred and heated to reflux and water removed by azeotropic distillation over temperature range 110° C.-115° C. The initial mixture was cloudy, but was observed to become clear at about 60° C. After 2.75 hours, the distillation was complete and 5.2 mL (milliliters) of water was collected (96% of theoretical amount). The reaction solution was cooled and filtered through a column of basic alumina (70 g; 150 mesh). The column was flushed with toluene (3×100 mL portions) and the filtrates were combined. The solvent was removed by distillation under reduced pressure and the crude ester was obtained as a viscous liquid (92.90 g; 99% yield). The crude material was dissolved in dichloromethane (380 mL) and the solution washed with a saturated solution of sodium bicarbonate (4×400 mL) followed by washing with deionized water (1×400 mL). The washed solution was dried over magnesium sulfate, filtered, and the solvent removed to yield the purified ester as a viscous liquid (80.29 g; 86% yield).

The structure of the product was confirmed by spectroscopic analyses to be the thiol-functional photo initiator (C): 1-[4-(2-{2'-mercaptopropionate}ethoxy)-phenyl]-2-hydroxy-2-methyl-1-propane-1-one. The results of NMR and IR analysis of the thiol-functional photoinitiator (C) product, is summarized as follows.

$^1$H NMR (300 MHz; CDCl$_3$): δ 8.06, d, 2H (Ar—H ortho C=O); δ 6.95, d, 2H (Ar—H meta C=O); δ 4.49, t, 2H (—CH$_2$—O—C=O); δ 4.21, t, 2H (—CH$_2$—O—Ar); δ 2.74, m, 4H (—S—CH$_2$—CH$_2$—C=O); δ 1.60, s, 6H (—C(CH$_3$)$_2$—); δ 1.70, s, 1H (—SH).

IR (thin film, ATR mode): 3474 cm$^{-1}$ (O—H); 2975 and 2934 cm$^{-1}$ (C—H); 2572 cm$^{-1}$ (S—H); 1736 cm$^{-1}$ (C=O ester); 1663 cm$^{-1}$ (C=O aromatic ketone).

Example-2

A macro-photoinitiator (E) according to the present invention was prepared in two stages, in accordance with the following description. In the first stage, a bromo-terminated poly(n-butyl acrylate) polymer (D) was prepared using a single electron transfer polymerization method. In the second stage, the bromo-terminated poly(n-butyl acrylate) polymer (D) was converted into the macro-photoinitiator (E) by substituting the terminal bromo groups with the thiol-functional photoinitiator (C) of Example-1. Synthesis of the macro-photoinitiator (E) is summarized in the following Synthetic Scheme-2.

The first stage (or Part-A) of the synthesis (i.e., synthesis of the bromo-terminated poly(n-butyl acrylate) polymer D) was conducted as follows. To a 30 mL cylindrical glass reactor fitted with a nitrogen inlet and mechanical stirrer having copper wire (0.1188 g; 1.87 mmoles; 0.1 mm diameter) wound around the blades of the stirrer was added n-butyl acrylate (6.029 g; 47.1 mmoles), dimethyl sulfoxide (DMSO; 3.002 g), and diethyl meso-2,5-dibromadipate (DEDBA; 0.4355 g; 1.21 mmoles). The mixture was stirred at room temperature until all the adipate initiator was dissolved, after which N,N,N',N'',N''-pentamethyldiethylenetriamine (PMDETA; 0.172 g; 0.994 mmoles) was added. The head space was swept with nitrogen to remove air, and the mixture was maintained under a slight positive pressure of nitrogen throughout the polymerization reaction. During the polymerization a blue-green color was observed to develop, and the mixture became progressively more viscous. After 24 hours stirring at room temperature, an aliquot of the reaction mixture was removed and analyzed by IR spectroscopy. The absorbance band at 805 cm$^{-1}$, characteristic of acrylate double bond, was completely absent from the spectrum and the absorbance band of the C=O carbonyl ester had shifted from 1724 cm$^{-1}$ to 1731 cm$^{-1}$, indicating that the unsaturated monomer was completely converted to the corresponding saturated polymer. The number average molecular weight ( Mn) of the polymer was calculated according to the known relationship for living polymerization at 100% conversion, using the following formula, $$\overline{Mn} = MW_M\left(\frac{[M]_0}{[I]_0}\right)(1.00) + MW_I$$

where $MW_M$ is the molecular weight of monomer (butyl acrylate), $[M]_0$ and $[I]_0$ represent the initial molar concentrations of monomer and initiator (DEDBA), respectively, and $MW_I$ is the molecular weight of the initiator. Accordingly the molecular weight of the bromo-terminated poly(n-butyl acrylate) polymer (D) was calculated to be 5,342.

Synthesis of the macro-photoinitiator (E) was conducted in the second stage (or Part-B) in accordance with the following description. Under yellow lighting, a portion of the polymer solution from the first stage (4.5216 g; 1.13 mmoles Br) was transferred to a 30 mL glass reactor, ethyl acetate (5 mL), and potassium carbonate (0.2707 g; 1.96 mmoles) were added. The mixture was stirred and thiol-functional photoinitiator (C) of Example-1 (0.5227 g; 1.68 mmoles) was added. The mixture was stirred at room temperature for 72 hours, filtered, and the solvent partially removed under reduced pressure. The residue was dissolved in ethyl acetate (15 mL) and a blend of methanol and water (10 mL; 1:1 vol/vol) added to precipitate the crude polymer product, which was obtained as a light blue colored viscous resin. The crude material was re-dissolved in ethyl acetate (10 mL) and washed with water (5 mL). The water layer was separated and extracted with ethyl acetate (2×10 mL portions). The combined ethyl acetate washings were dried over sodium sulfate, filtered, and the solvent removed to yield macro-photoinitiator (E) as a light yellow-colored viscous resin (2.660 g; 79% yield).

The structure and molecular weight of macro-photoinitiator (E) were confirmed by spectroscopic and chromatographic analyses, the results of which are summarized as follows.

$^1$H NMR (300 MHz; CDCl$_3$): δ 8.07, d, 4H (Ar—H ortho C═O); δ 6.96, d, 4H (Ar—H meta C═O); δ 4.45, t, 4H [(—CH$_2$—O—C(═O)— of ethyleneglycol end unit]; δ 4.3-3.9, m, 88H [(—CH$_2$—O—Ar and —CH2-O—C(═O)— of initiator and butyl repeat unit groups)]; δ 2.92, m, 4H (—S—CH$_2$—); δ 2.74, m, 4H [(—S—CH$_2$—CH$_2$—C(═O)—]; δ 2.28, broad m; 38H (—CH— backbone); 1.20-2.00 [C—CH$_2$—C backbone and butyl repeat unit groups, CH$_3$ ethyl group initiator fragment and —C(CH$_3$)$_2$—]; δ 0.95, t, 116H (—CH$_3$ butyl group). The number average molecular weight as determined by NMR was 5,760 and the corresponding theoretical value, calculated according to the procedure described in the first stage, was 5,804. As these values are very close and significantly different from the average molecular weight calculated for the intermediate dibromo polymer (D) (5,342; see first stage), it confirms that the polymer resulting from the second stage (i.e., macro-photoinitiator E) is formed by replacement of two bromine atoms of the intermediate dibromo polymer (D) of the first stage (160 mass units) with two thioether-linked photoinitiator groups (622 mass units).

GPC(PMMA calibration, THF, 1 mL/min): Average Mn=9,163, polydispersity (Mn/Mw)=1.20, for the macro-photoinitiator-(E).

Example-3

A macro-photoinitiator (G) according to the present invention was prepared in two stages, in accordance with the following description. In the first stage, a bromo-terminated polyacrylate terpolymer (F), containing residues of ethyl acrylate, 2-methoxyethyl acrylate, and butyl acrylate in a molar ratio of 5/3/2, was prepared using a single electron transfer polymerization method. In the second stage, the bromo-terminated polyacrylate terpolymer (F) was converted into the macro-photoinitiator (G) by substituting the terminal bromo groups with the thiol-functional photoinitiator (C) of Example-1. Synthesis of the macro-photoinitiator (G) is summarized in the following Synthetic Scheme-3.

Synthetic Scheme-3

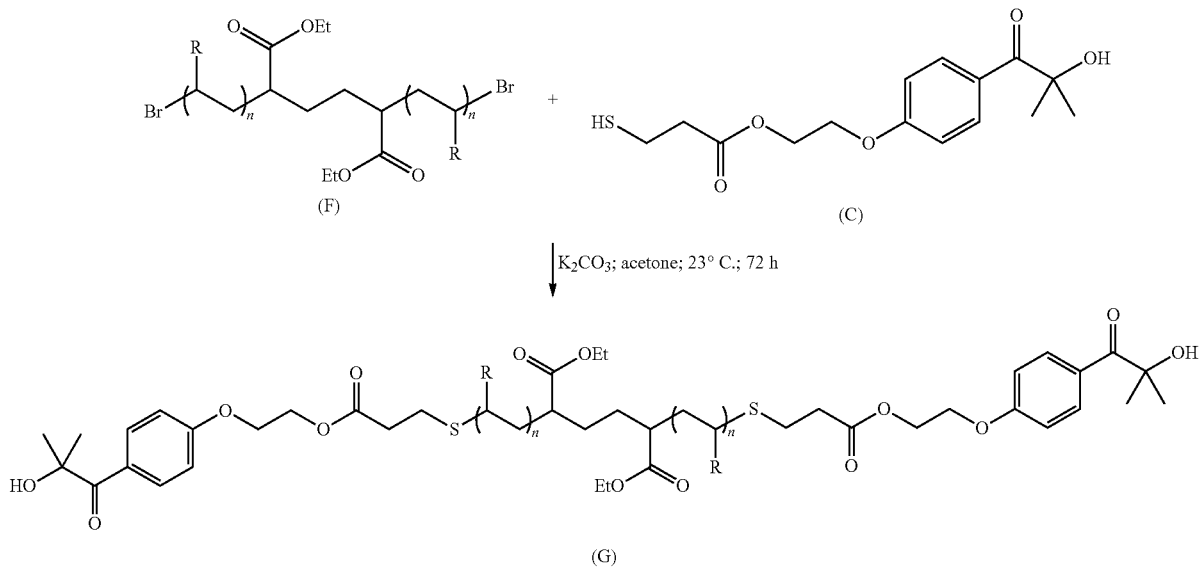

R = —COOR'
R' = ethyl; 2-methoxyethyl; or n-butyl.
n represents the average number of monomer residues
(each n may be the same or different).

The first stage (or Part-A) of the synthesis (i.e., synthesis of the bromo-terminated polyacrylate terpolymer F) was conducted as follows. To a 500-mL jacketed glass reactor fitted with a stainless steel propeller blade and shaft, dry-ice condenser, thermocouple, ATR infrared detector probe, and argon purge line was added ethyl acrylate (EA; 101.86 g; 1.02 moles), 2-methoxyethyl acrylate (MEA; 87.23 g; 0.67 moles), n-butyl acrylate (BA; 60.91 g; 0.48 moles), copper powder (0.32 g; <10 µm particle size), tris[2-(dimethylamino)ethyl]amine (0.058 g; 0.25 millimoles) (Me$_6$-TREN; prepared as described by M. Ciampolini, *Inorg. Chem.* 1966, 5 (1), 41), ethanol (99.42 g; 200 proof), and water (6.63 g). The mixture was stirred to give a homogeneous solution and cooled to 5° C. The reactor was evacuated at 15 torr under argon bleed and the vacuum released to argon atmosphere. The vacuum degassing step was repeated and diethyl meso-2,5-dibromoadipate (4.50 g; 12.50 millimoles) was added under positive pressure of argon. The reactor was sealed and vacuum degassed as previously described. The mixture was warmed to 25° C. and after 10 minutes a mild exotherm was observed as polymerization of the monomers occurred. Over the next 25 minutes the reaction temperature increased to 43° C. after which the exotherm subsided. The reaction mixture was stirred for a further 3 hours at 25° C. at which time the IR spectrum indicated 89% conversion of the monomers. Tetrahydrofuran (1,000 g) was added to the mixture and the light green-colored solution filtered through a column of neutral alumina (400 g) to provide a colorless solution. The solvents and residual monomers were removed by distillation under reduced pressure followed by heating under vacuum for 3 hours (40° C.; 650 mTorr) to yield the dibromo-terminated random terpolymer of ethyl acrylate, 2-methoxyethyl acrylate and n-butyl acrylate in mole proportions 5/3/2 as a viscous liquid (i.e., bromo-terminated polyacrylate terpolymer F) (198 g; 79% yield). The structure and composition of the polymer were confirmed by spectroscopic and chromatographic analyses. Using the formula discussed in Example-2, the theoretical number average molecular weight was calculated to be 18,144.

Synthesis of the macro-photoinitiator (G) was conducted in the second stage (or Part-B) in accordance with the following description. Under yellow lighting, a portion of the terpolymer (F) (5.203 g; 0.26 millimoles) was dissolved in acetone (12 mL) and the solution transferred to a 50 mL glass reaction flask fitted with a magnetic stirrer. A solution of the thiol-functional photoinitiator (C) of Example-1, in acetone (4.0 mL) was added to the stirred terpolymer (F) solution. Anhydrous potassium carbonate (0.237 g; 1.72 millimoles) and additional acetone (1 mL) were added and the mixture stirred at 23° C. for 72 hours. The reaction mixture was diluted with acetone (50 mL) and filtered. Solvent was removed from the filtrate by distillation under reduced pressure to yield macro-photoinitiator (G) in quantitative yield (5.32 g).

The structure and composition of macro-photoinitiator (G) were confirmed by spectroscopic and chromatographic analyses, the results of which are summarized as follows.

$^1$H NMR (300 MHz; CDCl$_3$): δ 8.07, d, 4H (Ar—H ortho C=O); δ 6.96, d, 4H (Ar—H meta C=O); δ 4.45, t, 4H [(—CH$_2$—O—C(=O)— of ethylene glycol end unit]; δ 4.3-3.9, m, 272H [(—CH$_2$—O—Ar and —CH2-O—C(=O)— of initiator and ester repeat unit groups)]; δ 3.56, t, 82H (—CH$_2$OCH$_3$ group of MEA); δ 3.35, s, 124H (—OCH$_3$ group of MEA); δ 3.0-2.6, broad m, 8H (—S—CH$_2$—CH$_2$—C(=O)—]; δ □2.15-2.50, m, 128H (—CH— backbone); δ □1.30-2.10, m, 438H [C—CH$_2$—C backbone and butyl repeat unit groups, CH$_3$ ethyl group initiator fragment, and —C(CH$_3$)$_2$—]; δ □1.25; t, 180H (—CH$_3$ of ethyl groups of EA units and initiator fragment); δ □0.95; t, 78H (—CH$_3$ of butyl groups of BA units).

GPC(PMMA calibration, THF, 1 mL/min): Average Mn=24,700, polydispersity=1.26 The relative molar proportion of BA/MEA/EA comonomer units in the polymer backbone was estimated to be 5.1/3.0/1.9 from the NMR spectrum. As these ratios are substantially similar to the monomer feed proportions employed (i.e., 4.7/3.1/2.2, Part A), it suggests that polymerization rates for each monomer were similar and the resulting terpolymer (F) and corresponding macro-photoinitiator (G) each have a random copolymer backbone architecture. In addition, the NMR spectrum confirms consumption of the 2-mercaptopropionate group of the thiol-functional photoinitiator (C) (disappearance of narrow multiplet centered at δ 2.74) and formation of corresponding 2-thiopropionate ether terminated polymer (G) (appearance of broad multiplet δ 2.6-3.0). The degree of end functionality, estimated from integral ratio δ 4.45/δ 4.3-3.9 (end group/repeat unit), was found to be approximately quantitative (i.e., 100% difunctional or 2 photoinitiator groups per polymer chain).

Example-4

A macro-photoinitiator (I) according to the present invention was prepared in two stages, in accordance with the following description. In the first stage, a bromo-terminated polyacrylate terpolymer (H), containing residues of butyl acrylate, ethyl acrylate, and 2-methoxyethyl acrylate in a molar ratio of 7.5/2.0/0.5, was prepared using a single electron transfer polymerization method. In the second stage, the bromo-terminated polyacrylate terpolymer (H) was converted into the macro-photoinitiator (I) by substituting the terminal bromo groups with the thiol-functional photoinitiator (C) of Example-1.

The first stage (or Part-A) of the synthesis (i.e., synthesis of the bromo-terminated polyacrylate terpolymer H) was conducted as follows. To a 6-L jacketed polymerization reactor fitted with a dry-ice condenser, mechanical stirrer, thermocouple, FTIR probe, argon purge, inlet port with rubber septum, vacuum line, and modified with an external catalyst chamber connected to the reactor by means of a peristaltic pump was added n-butyl acrylate (BA; 2,012 g; 15.70 moles), ethyl acrylate (EA; 419 g; 4.19 moles), 2-methoxyethyl acrylate (MEA; 136 g; 1.05 moles), acetone (2,135 g), water (142 g), and tris[2-(dimethylamino)ethyl]amine (1.0 g; 4.3 millimoles). The reaction mixture was stirred and cooled to 3° C. and a roll of knitted copper gauze (16.85 g), having a surface area of approximately 4.6 m$^2$/kg, was placed in the catalyst chamber. The system was purged with argon and dimethyl-2,6-dibromoheptanedioate (26.336 g; 0.076 moles) was added through the septum using a syringe. The stirred mixture was warmed to 27° C. and pumped through the external chamber containing the copper catalyst at a rate of 400 mL/minute to initiate polymerization of the monomers. The reaction temperature increased to 48° C. during the first hour of pumping and slowly decreased to 27° C. over the next three hours, at which stage another amount of tris[2-(dimethylamino)ethyl]amine (1.0 g; 4.3 millimoles) was added. The reaction was continued for an additional 4 hours, at which stage IR analysis indicated the conversion of monomers was 92%. The green-colored solution was filtered through a bed of neutral alumina (100 g) to remove dissolved copper salts and the solvents and residual monomers were removed by distillation under reduced pressure to give a dibromo-terminated random terpolymer (H) of butyl acrylate, ethyl acrylate, and 2-methoxyethyl acrylate in mole proportions 7.5/2.0/0.5 as a near-colorless viscous liquid (2,145 g; 83% yield). The number average molecular weight, calculated using the formula of Example-2, was determined to be 31,400.

The structure and composition of the intermediate terpolymer (H) were confirmed by $^1$H NMR spectroscopic and chromatographic analyses, the results of which are summarized as follows.

$^1$H NMR (300 MHz; CDCl$_3$): The spectrum shows signals characteristic of a polyacrylate backbone with chemical shifts, integration values, multiplicity, and assignments as follows: δ 4.3-3.9, m, 510H [(—CH2-O—C(═O)— of ester repeat unit groups)]; δ 3.67, s, 4.32H (—OCH$_3$ pimelate initiator) δ 3.60, t, 17H (—CH$_2$OCH$_3$ group of MEA); δ 3.40, s, 30H (—OCH$_3$ group of MEA); δ 2.25-2.45, m, 234H (—CH— backbone); δ □1.25-2.25, m, 1430H (C—CH$_2$—C groups in backbone, BA repeat units and initiator fragment and CH$_3$ in EA units); δ 0.95; t, 597H (—CH$_3$ of butyl groups of BA units). The number average molecular weight (Mn) and relative molar proportions of BA/EA/MEA were estimated to be 39,700 and 7.8/1.8/4.0, respectively. SEC (THF; 1 mL/min; RI detector): average $M_n$ (PMMA calibration)=35, 300; PD=1.09.

Synthesis of the macro-photoinitiator (I) was conducted in the second stage (or Part-B) in accordance with the following description. A solution of the bromo-terminated terpolymer (H) (1000 g; 0.032 moles) in acetone (1,000 mL) was added to 3-L glass jacketed reactor fitted with mechanical stirrer, thermocouple, and inlet port. To this solution, under yellow lights, was added the thiol-functional photoinitiator (C) of Example 1 (24.84 g; 0.080 moles) and potassium carbonate (10.99 g; 0.080 moles). The mixture was stirred at 27° C. for 72 hours and filtered under pressure through a layered bed of CELITE diatomite (100 g) and alumina (500 g) to remove solids. The solvent was removed under reduced pressure to yield corresponding terpolymer (810 g; 79% yield) in which the bromine groups were substituted by the thiol groups of the thiol-functional photoinitiator (C). The number average molecular weight of the resulting polymer (I) was calculated to be 31,900.

The structure and composition of the macro-photoinitiator (I) were confirmed by 1H NMR and size exclusion chromatography (SEC), the results of which are summarized as follows.

$^1$H NMR (300 MHz; CDCl$_3$): δ 8.07, d, 4H (Ar—H ortho C═O); δ 6.96, d, 4H (Ar—H meta C═O); δ 4.45, t, 4H [(—CH$_2$—O—C(═O)— of ethylene glycol end unit]; δ 4.47, t, (4H) [(—CH$_2$—O—C(═O)— of ethylene glycol end unit]; δ 4.3-3.9, m, 562H [(—CH$_2$—O—Ar and —CH$_2$—O—C(═O)— of ester repeat unit groups)]; δ 3.63, s, 8H (—OCH$_3$ of initiator fragment); δ 3.50, t, 24H (—CH$_2$OCH$_3$ group of MEA); δ 3.32, s, 34H (—OCH$_3$ group of MEA); δ 3.0-2.6, broad m, (12H)(—S—CH$_2$—CH$_2$—C(═O)—]; δ 2.17-2.48, m, 267H (—CH— backbone); δ 1.30-2.10, m, 1609H [C—CH$_2$—C backbone and BA repeat unit groups, CH$_3$ ethyl group initiator fragment, EA units and —C(CH$_3$)$_2$—]; δ 0.95; t, 597H (—CH$_3$ of butyl groups of BA units). The number average molecular weight and mole proportions of BA/EA/MEA were estimated to be 32,600 and 7.5/0.4/2.1, respectively. SEC (THF; 1 mL/min; RI detector): Mn=37,200; PD=1.11.

Comparative size exclusion chromatographic (SEC) analysis of the intermediate bromo-terminated polyacrylate terpolymer (H) and the corresponding macro-photoinitiator (I) of Example-4 were carried out using in-line refractive index and UV detectors.

Figure 4A:
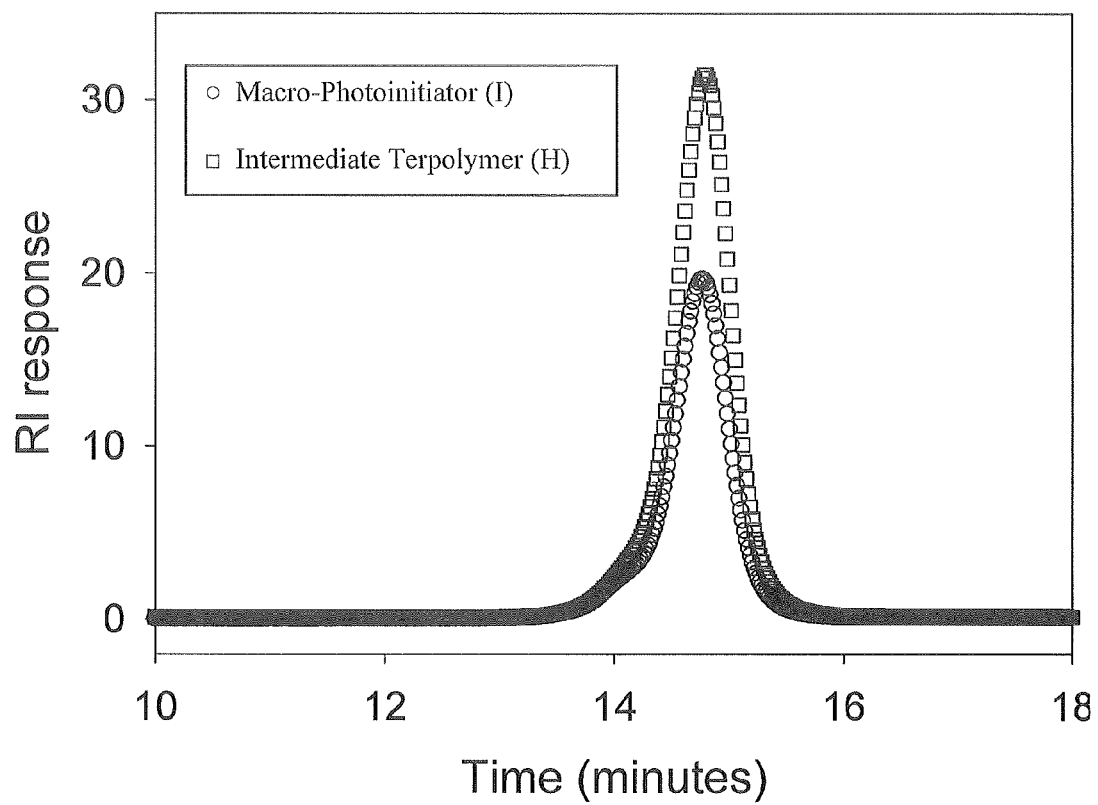
FIG. 4(a) is a graphical representation of the comparative size exclusion chromatographic analysis of the intermediate bromo-terminated terpolymer (H) and the related macro-photoinitiator (I) of Example 4, in which the refractive index response is plotted as a function of time.
Figure 4B:
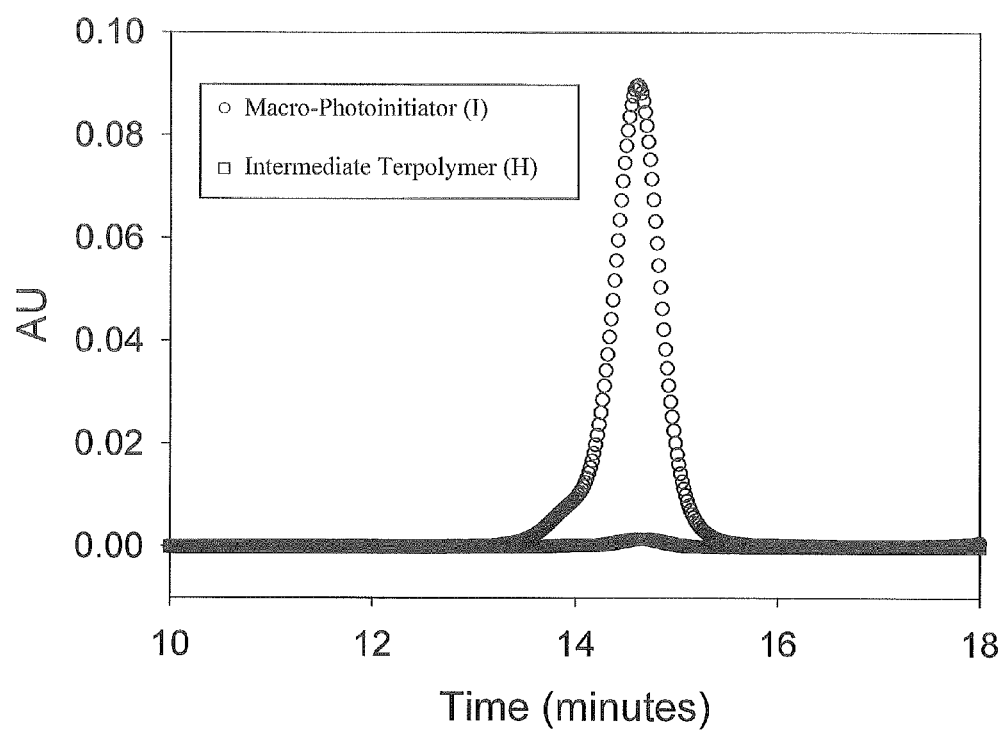
FIG. 4(b) is a graphical representation of the comparative size exclusion chromatographic analysis of the intermediate bromo-terminated terpolymer (H) and the related macro-photoinitiator (I) of Example 4, in which the ultraviolet response is plotted as a function of time.

The wavelength of UV detection was selected at 270 nm, which corresponds to an intense π-π* transition associated with the aromatic ketone of macro-photoinitiator (I). While the refractive index responses of both polymers were expected to be comparable (e.g., due to similar molecular weights and composition) the UV responses at 270 nm were expected to differ significantly due to the presence of the aromatic ketone group in macro-photoinitiator (I). The GPC results clearly demonstrated the differences between the two polymer structures. See FIGS. 4(a) and 4(b) of the drawings. The refractive index responses of both polymers were similar, showing raised peaks at similar elusion times. See FIG. 4(a). In contrast, the UV responses differed significantly. See FIG. 4(b) The macro-photoinitiator (I) showed a very strong response (i.e., peak) corresponding to the elution time from the refractive index detector. The intermediate bromo-terminated polyacrylate terpolymer (H), however, showed no significant response in the UV (maintaining a substantially baseline trace over the whole of the elution time). See FIG. 4(b). These observations confirm that the macro-photoinitiator (I) of Example-4 had photoinitiator groups attached to the terminal portions of the polymer chain.

Comparative Example-1

A comparative terpolymer (J) having terminal acrylate groups, rather than terminal photoinitiator groups derived from thiol-functional photoinitiator (C), was prepared in two stages, in accordance with the following description. In the first stage, a bromo-terminated polyacrylate terpolymer (F), containing residues of ethyl acrylate, 2-methoxyethyl acrylate, and butyl acrylate in a molar ratio of 5/3/2, was prepared using a single electron transfer polymerization method, as described in the first stage (or Part-A) of Example-3. In the second stage, the bromo-terminated polyacrylate terpolymer (F) was converted into the comparative terpolymer (J) by substituting the terminal bromo groups with a sodium salt of acrylic acid. Synthesis of the comparative terpolymer (J) is summarized in the following Synthetic Scheme-4.

Synthetic Scheme-4

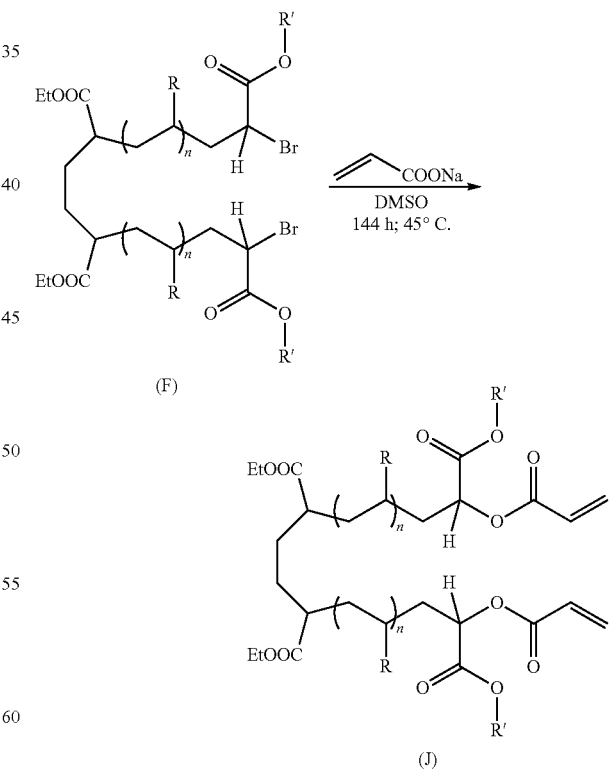

R = ——COOR'
R' = ethyl; 2-methoxyethyl; or n-butyl.
n represents the average number of monomer residues (each n may be the same or different).

To a 5-L glass reactor equipped with a mechanical stirrer and a double turbine blade, thermocouple, reflux condenser, and heating mantel was added 4-methoxyphenol (0.32 g; 0.026 moles), dibromo-terminated acrylate terpolymer (F) having molecular weight 20,400, and polydispersity 1.30 (prepared using DMSO as solvent by the procedure described in Part A of Example 4) (1,546.00 g), and DMSO (2,319 g). The mixture was stirred and heated at 45° C. for about one hour to dissolve the polymer, after which pulverized sodium acrylate (73.45 g; 0.78 moles) was added. Heating and stirring were continued for an additional 144 hours. CELITE diatomite (45 g) was added, the mixture stirred for 25 minutes and filtered under pressure. The filtrate was transferred to a distillation flask and concentrated on a rotary evaporator by removal of 772 g of DMSO (70° C. and about 20 torr). The concentrated solution was transferred to a 12-L flask fitted with mechanical stirrer, diluted with 3.3 L dichloromethane and washed with 3×3.3 L water. The dichloromethane solution was processed in a centrifuge at 2,000 rpm for 30 minutes and residual water separated. Magnesium sulfate (150 g) was added, the mixture filtered under pressure, and the solvent removed under reduced pressure to yield a slightly hazy, liquid polymer having acrylate groups substituted at the chain ends (1,202 g; 78% yield).

The structure and composition of comparative terpolymer (J) were confirmed by infrared and $^1$H NMR spectroscopy and size exclusion chromatography, the results of which are summarized as follows. The average number of terminal acrylate groups per polymer chain was estimated from NMR spectrum to be 1.9.

IR (ATR mode): 1727 cm$^{-1}$ ester carbonyl of polyacrylate.
$^1$H NMR (300 MHz; CDCl$_3$): δ 6.45, d, 2H (C1 terminal alkene; cisoid); δ 6.15, m, 1H (C2 terminal alkene); δ 5.90, d, 2H (C1 terminal alkene; transoid); δ 5.00, m, 2H (C4 methine, α-ester); δ 3.90-4.30, m, 309H (—OCH$_2$—) (Estimated average M$_n$ from NMR spectrum=18,200) SEC (THF; 1 mL/min; RI detector): average M$_n$ (PMMA calibration)= 20,600; polydispersity=1.30 (monomodal distribution).

Example-A

A curable composition including the macro-photoinitiator (E) of Example-2 was prepared and cured by exposure to actinic radiation in accordance with the following description. An ultraviolet light (UV) sensitive composition was prepared under yellow lighting by blending 0.065 g of the macro-photoinitiator (E) of Example-2 with 0.603 g 1,6-hexanediol diacrylate. The macro-photoinitiator (E) readily dissolved in the 1,6-hexanediol diacrylate to provide a clear solution. Drops of the resulting curable composition approximately 1 mm in thickness were placed on microscope slides and positioned 2.0 cm below the tip of a wand from a ZETA 7730 UV lamp and exposed to UV light for 5 seconds. Using a calibrated UV Puck radiometer, the incident UV light intensity at the surface of the slides was found to be 0.23 W/cm$^2$ (UVA), 0.01 W/cm$^2$ (UVB), 0.0 W/cm$^2$ (UVC), and 0.22 W/cm$^2$ (UVV). In all cases the liquid drops were found to have cured to hard clear plastic solids, and were insoluble in acetone. In contrast, drops of 1,6-hexanediol alone failed to cure when exposed to ultraviolet (UV) light under the same conditions. The results demonstrate that curable compositions containing the macro-photoinitiators according to the present invention are efficiently curable upon exposure to actinic radiation, such as UV light.

Examples-B and C

Curable compositions including the macro-photoinitiator (G) of Example-3 were prepared and cured by exposure to actinic radiation in accordance with the following description. Curable liquid compositions were prepared under yellow lighting by blending together the components listed in Table 1. The liquid materials were cast into shallow rectangular aluminum molds 1 cm×2 cm and 0.5 mm in depth, and exposed to UV light from a ZETA 7216 lamp system fitted with a Fusion Systems H-bulb for 30 seconds. The incident light intensity was measured at 180 mW/cm$^2$ (UVA). Both formulations cured rapidly to provide solid products (or polymerizates) that were insoluble in acetone.

TABLE 1

| Ingredients | Example-B | Example-C |
| --- | --- | --- |
| Macro-photoinitiator (G) Of Example 3 | 78.2 | 73.4 |
| Poly(propylene glycol diacrylate) (Mn = 900) | 7.6 | 0 |
| 2-ethylhexyl acrylate | 14.2 | 0 |
| 1,6-hexanediol diacrylate | 0 | 26.6 |
| Cured state | Soft gel | Strong elastomer |

The cured state results summarized in Table-2 demonstrate that curable compositions containing a macro-photoinitiator according to the present invention are efficiently cured by exposure to actinic radiation, such as UV light, and that by selection of reactants having at least one ethylenically unsaturated radically polymerizable group, e.g., poly(propylene glycol diacrylate), 2-ethylhexyl acrylate, or 1,6-hexanediol diacrylate, the properties of the resulting cured product (or polymerizate) can be predictably controlled.

Examples-D and E

Curable compositions including the macro-photoinitiator (G) of Example-3 and comparative terpolymer (J) of Comparative Example-1 were prepared by blending the ingredients as summarized in Table-2 below.

TABLE 2

| Ingredients | Example-D | Example-E |
| --- | --- | --- |
| Macro-photoinitiator (G) Of Example 3 | 73 | 0 |
| Comparative terpolymer (J) Of Comparative Example 1 | 0 | 78 |
| 1,6-hexanediol diacrylate | 27 | 20 |
| DARACUR 1173 Photoinitiator | 0 | 2 |

In Table-2, DARACUR 1173 photoinitiator chemically is 2-hydroxy-2-methyl-1-phenylpropan-1-one, which is commercially available from Ciba Specialty Chemicals. The amount of added photoinitiator in Example-E was selected to correspond to the molar concentration of the terminal photoinitiator groups of macro-photoinitiator (G) of Example-D (i.e., 0.12 moles/liter). Since the photoactive chromophores of Examples-D and E are structurally the same and present in equal amounts, the absorbance or optical densities of both compositions are similar. The concentrations of acrylate groups are similar (2.4 equivalents acrylate/liter for Example-D, and 1.8 equivalents acrylate/liter for Example-E).

The photocuring response of Examples-D and E was investigated using an oscillatory photorheometer. In these evaluations a sinusoidal strain deformation was applied to a uniform film (1.00 mm in film thickness) of the compositions confined between a fixed UV-transparent glass plate (e.g., quartz) and an oscillating aluminum plate and the resulting shear was monitored. The initial strain was applied at a frequency of 1 Hz and strain amplitude of 1% (linear viscoelastic region). After a steady-state response was established (16 seconds), the film was exposed to UV light from a mercury lamp source, transmitted through a light guide located directly below the transparent plate of the rheometer. The UV dose and exposure time were controlled by means of attenuation filters and an electronic shutter. The filters were adjusted to give an incident UV light intensity of 8 mW/cm$^2$ at the film surface, as measured by a calibrated radiometer with peak sensitivity at 365 nm.

Using the above-described technique, changes in mechanical properties as a result of UV light exposure were monitored in real-time. The complex modulus (G*) relates to (or tracks) the out-of-phase viscous or liquid response (loss modulus, G") before gelation and the in-phase elastic or solid response (storage modulus, G') after the polymer network has been formed. The gel point is estimated from the crossover of viscous and elastic moduli (i.e., when phase angle is 45°). As demonstrated by FIG. 1 of the drawings, the changes in G* that occur during UV exposure are large (about 4 orders of magnitude). Examples-D and E have comparable viscosities before exposure: G* at 10s=0.6 and 0.3 KPa for Examples-D and E, respectively. However, after curing, the properties are significantly different. Example-D has a shear modulus at 100 s of 4.7 MPa, whereas the corresponding value for Example-E is 1.9 MPa. The result indicates that the polymer with terminal photoinitiator groups (i.e., macro-photoinitiator G) is more efficiently incorporated into the polymer network than is the corresponding polymer with acrylate end-substitution (i.e., comparative terpolymer J). In addition, it demonstrates that initiating polymerization from a polymer chain end (e.g., grafting from), using a macro-photoinitiator according to the present invention (e.g., macro-photoinitiator G) is more advantageous with regard to achieving desirable mechanical properties than is the comparative approach of using an un-tethered photoinitiator and grafting-through a polymer bound ethylenically unsaturated and radically polymerizable end-group (e.g., as with the terminal acrylate groups of comparative terpolymer J).

Figure 2:
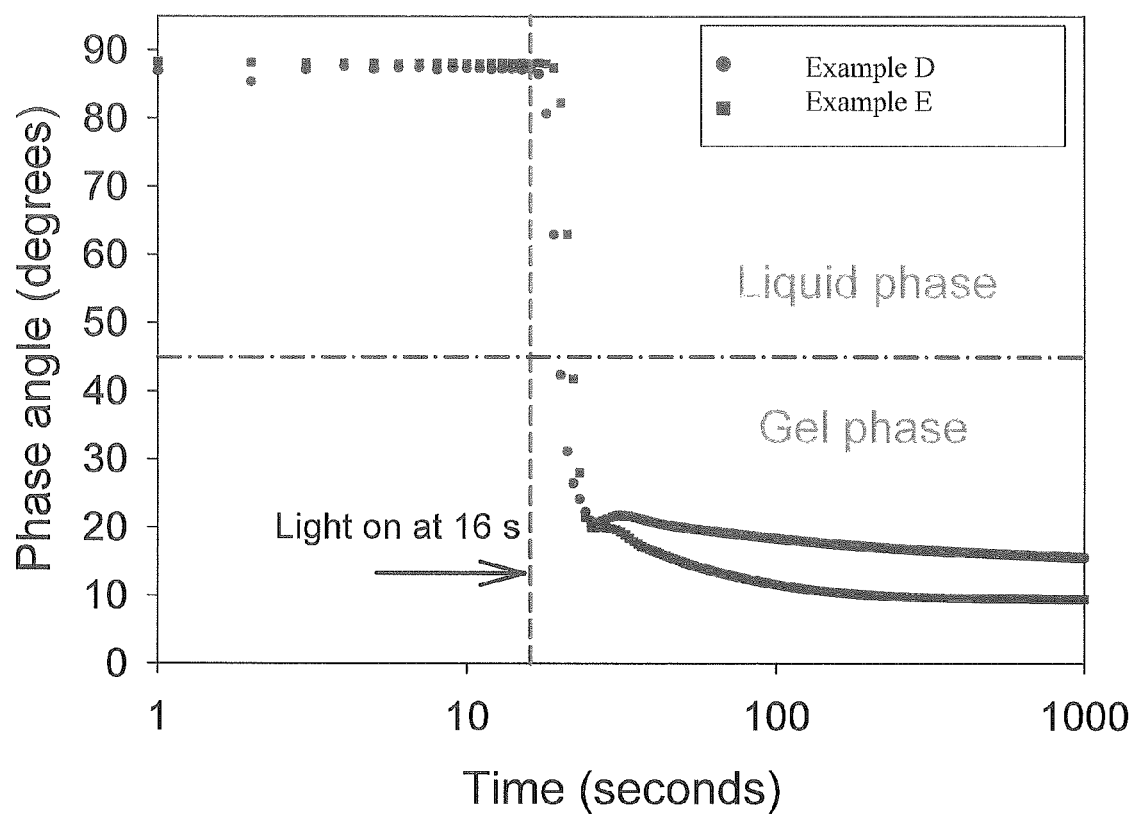
FIG. 2 is a graphical representation of phase angle as a function of time during UV curing of compositions according to Examples D and E.

With reference to FIG. 2 of the drawings, the corresponding phase angle changes that occur during photo-curing of the compositions of Examples-D and E is demonstrated. Before exposure to UV light both compositions are stable liquids, but shortly after illumination the phase angles rapidly decrease, as the liquid materials form gelled products (i.e., phase angle<45°).

The photocuring rate can be estimated from the time required to form a gel or network structure from the initial exposure. With further reference to FIG. 2, the gel time for Example-D was 4 seconds, while that of Example-E was 6 seconds. This result indicates that photosensitivity is improved by the use of macro-photoinitiators according to the present invention. The result is particularly surprising since polymers having reactive groups, such as photopolymerizable groups, bound thereto, are generally observed to react more slowly than comparable low molar mass compounds at similar concentrations, due to reduced molecular mobility and increased diffusion rates associated with the higher mass polymer materials.

Figure 3:
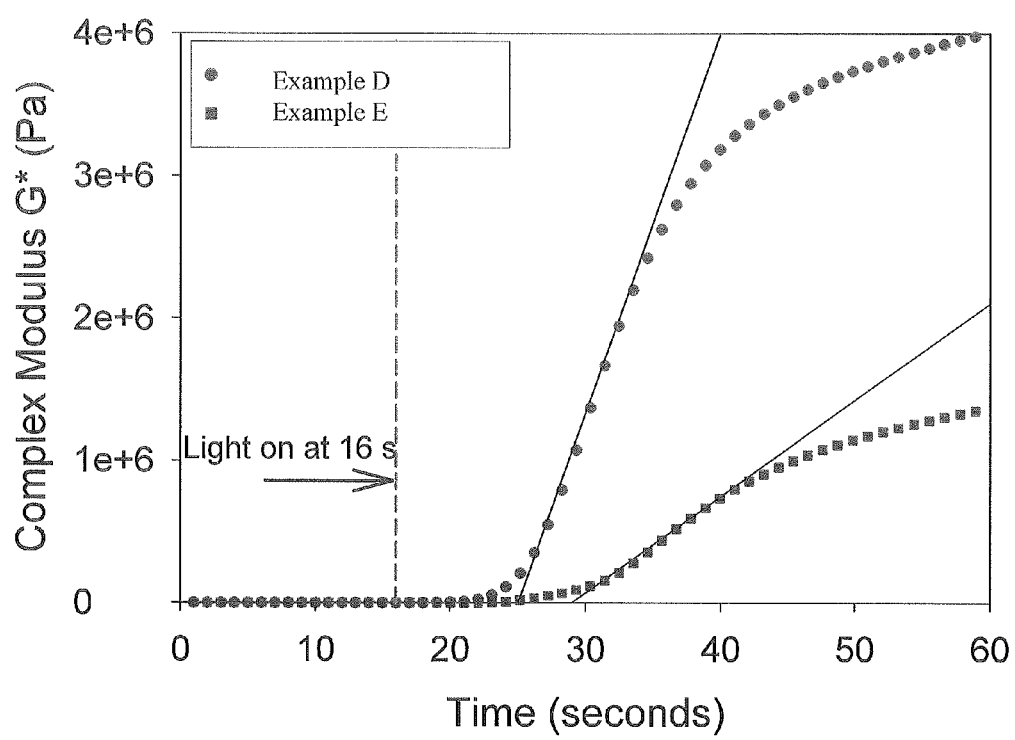
FIG. 3 is a graphical representation of the plot of FIG. 1, focusing on the time shortly after initial exposure of the photo-curable compositions to UV light, and further including projected tangent lines superimposed on the initial modulus curves.

A more accurate estimate of the curing rates may be obtained by a closer examination of rheometric data in the time immediately following the initial exposure. With reference to FIG. 3 of the drawings, clearly defined induction times are observed directly following initial exposure to UV light, during which there is no significant build-up of modulus, despite the very rapid gelation. The induction times were determined by projecting (or extending) the tangent lines to the linear portion of the initial modulus curve onto the time axis (i.e., the x-axis), as shown in FIG. 3. By this method, induction times of 9 seconds (Example-D) and 13 seconds (Example-E) were determined. The relative curing rates were then estimated from the slopes of the tangent lines, and were found to be 3.9 (Example-D) and 1.0 (Example-E). The desirably enhanced photosensitivity of macro-photoinitiators according to the present invention discussed with reference to FIG. 2, was thus more accurately confirmed with reference to FIG. 3.

The present invention has been described with reference to specific details of particular embodiments thereof. It is not intended that such details be regarded as limitations upon the scope of the invention except insofar as and to the extent that they are included in the accompanying claims.

The invention claimed is:

1. A macro-photoinitiator comprising a polymer chain structure represented by the following general formula (I),

Φ-[[-(M)$_p$-]$_x$-Y-L-PI]$_z$ (I)

wherein,
Φ is a residue of a polymerization initiator,
M is a residue of at least one ethylenically unsaturated radically polymerizable monomer,
p represents an average number of monomer residues occurring in a block of monomer residues,
p, x, and z are each individually selected such that said macro-photoinitiator has a number average molecular weight of at least 400,
p is, independently for each x, an integer from 1 to 5000,
x is, independently for each z, an integer from 1 to 20,
z is at least 1,
Y, independently for each z, is selected from S and O,
L, independently for each z, is a bond or a divalent linking group comprising at least one divalent moiety selected from the group consisting of divalent organic moieties, divalent inorganic moieties, and combinations thereof, and
PI, independently for each z, represents a photoinitiator residue,
wherein said photoinitiator residue is selected from the group consisting of triazine residues, fluorenone residues, and residues represented by the following general formula (II),

(II)

wherein, R is aryl, aryl substituted with at least one substituent selected from the group consisting of $C_1$-$C_{20}$ alkyl, halogen and combinations thereof, $C_3$-$C_{12}$ cycloalkyl or —$CR_1R_2R_3$, wherein $R_1$, $R_2$ and $R_3$ are each individually selected from the group consisting of hydrogen, hydroxyl, aryl, aryl substituted with at least one substituent selected from the group consisting of $C_1$-$C_{20}$ alkyl, halogen, and combinations thereof, $C_1$-$C_{20}$ hydroxylalkyl, $C_1$-$C_{20}$ alkoxy, $C_3$-$C_{12}$ cycloalkyl, and —C(O)—$R_5$, wherein $R_5$ is aryl or aryl substituted with at least one substituent selected from the group consisting of $C_1$-$C_{20}$ alkyl, halogen and combinations thereof, and $R_4$ in each instance is independently selected from the group consisting of hydrogen, halogen, linear, or branched $C_1$-$C_{20}$ alkyl, $C_3$-$C_{12}$ cycloalkyl, and aryl.

2. The macro-photoinitiator of claim 1, wherein,
Φ is selected from the group consisting of linear or branched aliphatic compounds, cycloaliphatic compounds, heterocyclic compounds, aryl compounds, heteroaryl compounds, aralkyl compounds, sulfonyl compounds, sulfenyl compounds, esters of carboxylic acids, polymeric compounds, and mixtures thereof,
z is from 1 to 10,
said macro-photoinitiator has a number average molecular weight of from 400 to 500,000, and a polydispersity index of less than 1.8,
L is said divalent linking group comprising at least one divalent organic moiety and optionally at least one divalent inorganic moiety selected from the group consisting of —O—, —C(O)—, —O—C(O)—, —O—C(O)—O—, and combinations thereof.

3. The macro-photoinitiator of claim 2, wherein,
said photoinitiator residue is selected from photoinitiator residues represented by general formula (II),
—Y-L- is represented by the following general formula (IIIa),

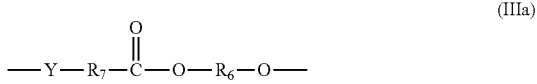
(IIIa)

wherein $R_6$ is a divalent organic moiety, and $R_7$ is a bond or a divalent organic moiety,
R is —$CR_1R_2R_3$,
$R_1$ is selected from hydrogen or hydroxyl,
$R_2$ and $R_3$ are each independently selected from linear or branched $C_1$-$C_{20}$ alkyl, and
$R_4$ in each instance is independently selected from hydrogen, and linear or branched $C_1$-$C_{20}$ alkyl.

4. The macro-photoinitiator of claim 3, wherein
Y is S,
M is derived from at least one of vinyl monomers, allylic monomers and olefins,
$R_1$ is hydroxyl,
$R_2$ and $R_3$ are each independently selected from linear or branched $C_1$-$C_6$ alkyl,
$R_4$ is hydrogen, and
$R_6$ and $R_7$ are each independently selected from divalent linear or branched $C_1$-$C_6$ alkylene.

5. The macro-photoinitiator of claim 4, wherein
M is derived from at least one of alkyl (meth)acrylates having from 1 to 20 carbon atoms in the alkyl group, vinyl aromatic monomers, vinyl halides, vinyl esters of carboxylic acids, olefins, acrylonitrile, methacrylonitrile, N,N-di($C_1$-$C_6$ alkyl)-(meth)acrylamide, and mixtures thereof, and
z is from 1 to 5.

6. The macro-photoinitiator of claim 1, wherein said macro-photoinitiator is prepared by a controlled radical polymerization method.

7. The macro-photoinitiator of claim 6, wherein said controlled radical polymerization method is selected from atom transfer radical polymerization and single electron transfer polymerization.

8. The macro-photoinitiator of claim 6, wherein said initiator has at least one radically transferable group, said residue of said polymerization initiator, Φ, is free of said radically transferable group, and z is from 1 to the average total number of radically transferable groups of said initiator.

9. The macro-photoinitiator of claim 8, wherein said polymerization initiator is selected from the group consisting of halomethane, methylenedihalide, haloform, carbon tetrahalide, methanesulfonyl halide, p-toluenesulfonyl halide, methanesulfenyl halide, p-toluenesulfenyl halide, 1-phenylethyl halide, $C_1$-$C_6$-alkyl ester of 2-halo-$C_1$-$C_6$-carboxylic acid, p-halomethylstyrene, mono-hexakis(alpha-halo-$C_1$-$C_6$-alkyl)benzene, di($C_1$-$C_6$-alkyl)-2-halo-2-methyl malonate, $C_1$-$C_6$-alkyl 2-haloisobutyrate, di($C_1$-$C_6$-alkyl)-2,5-dihaloadipate, and mixtures thereof.

10. The macro-photoinitiator of claim 1, wherein
said macro-photoinitiator has gross polymer architecture selected from the group consisting of linear polymer architecture, branched polymer architecture, hyperbranched polymer architecture, and star polymer architecture, and
said macro-photoinitiator has backbone architecture selected from the group consisting of homopolymer backbone architecture, random copolymer backbone architecture, block copolymer backbone architecture, and gradient copolymer backbone architecture.

11. A curable composition comprising:
(a) a macro-photoinitiator comprising a polymer chain structure represented by the following general formula (I), $$\Phi\text{-}[[\text{-}(M)_p\text{-}]_x\text{-}Y\text{-}L\text{-}PI]_z \qquad (I)$$

wherein,
Φ is a residue of a polymerization initiator,
M is a residue of at least one ethylenically unsaturated radically polymerizable monomer,
p represents an average number of monomer residues occurring in a block of monomer residues,
p, x, and z are each individually selected such that said macro-photoinitiator has a number average molecular weight of at least 400,
p is, independently for each x, an integer from 1 to 5000,
x is, independently for each z, an integer from 1 to 20,
z is at least 1,
Y, independently for each z, is selected from S and O,
L, independently for each z, is a bond or a divalent linking group comprising at least one divalent moiety selected from the group consisting of divalent organic moieties, divalent inorganic moieties, and combinations thereof, and
PI, independently for each z, represents a photoinitiator residue,
wherein said photoinitiator residue is selected from the group consisting of triazine residues, fluorenone residues, and residues represented by the following general formula (II),

(II)

wherein, R is aryl, aryl substituted with at least one substituent selected from the group consisting of $C_1$-$C_{20}$ alkyl, halogen and combinations thereof, $C_3$-$C_{12}$ cycloalkyl or —$CR_1R_2R_3$, wherein $R_1$, $R_2$ and $R_3$ are each individually selected from the group consisting of hydrogen, hydroxyl, aryl, aryl substituted with at least one substituent selected from the group consisting of $C_1$-$C_{20}$ alkyl, halogen and combinations thereof, $C_1$-$C_{20}$ hydroxylalkyl, $C_1$-$C_{20}$ alkoxy, $C_3$-$C_{12}$ cycloalkyl, and —C(O)—$R_5$, wherein $R_5$ is aryl or aryl substituted with at least one substituent selected from $C_1$-$C_{20}$ alkyl, halogen and combinations thereof, and R$_4$ in each instance is independently selected from the group consisting of hydrogen, halogen, linear or branched C$_1$-C$_{20}$ alkyl, C$_3$-C$_{12}$ cycloalkyl, and aryl; and (b) at least one reactant comprising at least one ethylenically unsaturated radically polymerizable group.

12. The curable composition of claim 11, wherein
Φ is selected from the group consisting of linear or branched aliphatic compounds, cycloaliphatic compounds, heterocyclic compounds, aryl compounds, heteroaryl compounds, aralkyl compounds, sulfonyl compounds, sulfenyl compounds, esters of carboxylic acids, polymeric compounds, and mixtures thereof, z is from 1 to 10, said macro-photoinitiator has a number average molecular weight of from 400 to 500,000, and a polydispersity index of less than 1.8, L is said divalent linking group comprising at least one divalent organic moiety and optionally at least one divalent inorganic moiety selected from the group consisting of —O—, —C(O)—, —O—C(O)—, —O—C(O)—O—, and combinations thereof.

13. The curable composition of claim 12, wherein
said photoinitiator residue is selected from photoinitiator residues represented by general formula (II),
—Y-L- is represented by the following general formula (IIIa), $$-Y-R_7-\overset{\overset{\displaystyle O}{\|}}{C}-O-R_6-O- \qquad \text{(IIIa)}$$

wherein R$_6$ is a divalent organic moiety, and R$_7$ is a bond or a divalent organic moiety, R is —CR$_1$R$_2$R$_3$, R$_1$ is selected from hydrogen or hydroxyl, R$_2$ and R$_3$ are each independently selected from linear or branched C$_1$-C$_{20}$ alkyl, and R$_4$ in each instance is independently selected from hydrogen, and linear or branched C$_1$-C$_{20}$ alkyl.

14. The curable composition of claim 13, wherein
Y is S,
M is derived from at least one of vinyl monomers, allylic monomers and olefins,
R$_1$ is hydroxyl,
R$_2$ and R$_3$ are each independently selected from linear or branched C$_1$-C$_6$ alkyl,
R$_4$ is hydrogen, and
R$_6$ and R$_7$ are each independently selected from divalent linear or branched C$_1$-C$_6$ alkylene.

15. The curable composition of claim 14, wherein
M is derived from at least one of alkyl (meth)acrylates having from 1 to 20 carbon atoms in the alkyl group, vinyl aromatic monomers, vinyl halides, vinyl esters of carboxylic acids, olefins, acrylonitrile, methacrylonitrile, N,N-di(C$_1$-C$_6$ alkyl)-(meth)acrylamide, and mixtures thereof, and
z is an integer from 1 to 5.

16. The curable composition of claim 11, wherein said macro-photoinitiator is prepared by controlled radical polymerization.

17. The curable composition of claim 16, wherein said controlled radical polymerization method is selected from atom transfer radical polymerization and single electron transfer polymerization.

18. The curable composition of claim 16, wherein said initiator, of said macro-photoinitiator, has at least one radically transferable group, said residue of said initiator, Φ, is free of said radically transferable group, and z is from 1 to the average total number of radically transferable groups of said initiator.

19. The curable composition of claim 18, wherein said initiator is selected from the group consisting of halomethane, methylenedihalide, haloform, carbon tetrahalide, methanesulfonyl halide, p-toluenesulfonyl halide, methanesulfenyl halide, p-toluenesulfenyl halide, 1-phenylethyl halide, C$_1$-C$_6$-alkyl ester of 2-halo-C$_1$-C$_6$-carboxylic acid, p-halomethylstyrene, mono-hexakis(alpha-halo-C$_1$-C$_6$-alkyl)benzene, di(C$_1$-C$_6$-alkyl)-2-halo-2-methyl malonate, C$_1$-C$_6$-alkyl 2-haloisobutyrate, di(C$_1$-C$_6$-alkyl)-2,5-dihaloadipate, and mixtures thereof.

20. The curable composition of claim 11, wherein
said macro-photoinitiator has gross polymer architecture selected from the group consisting of linear polymer architecture, branched polymer architecture, hyperbranched polymer architecture, and star polymer architecture, and
said macro-photoinitiator has backbone architecture selected from the group consisting of homopolymer backbone architecture, random copolymer backbone architecture, block copolymer backbone architecture, and gradient copolymer backbone architecture.

21. The curable composition of claim 11, wherein said reactant comprises a monomer selected from the group consisting of vinyl monomers, allylic monomers, olefins, and combinations thereof.

22. The curable composition of claim 21, wherein said monomer, of said reactant, comprises at least one of alkyl (meth)acrylates having from 1 to 20 carbon atoms in the alkyl group, vinyl aromatic monomers, vinyl halides, vinyl esters of carboxylic acids, olefins, acrylonitrile, methacrylonitrile, N,N-di(C$_1$-C$_6$ alkyl)-(meth)acrylamide, and mixtures thereof.

23. The curable composition of claim 11, wherein said curable composition is a curable adhesive composition.

24. The curable composition of claim 11, wherein said curable composition is a curable molding composition.

25. The curable composition of claim 11, wherein said curable composition is curable by exposure to actinic radiation.

26. A macro-photoinitiator comprising a polymer chain structure represented by the following general formula (I), $$\Phi\text{-}[[\text{-}(M)_p\text{-}]_x\text{-}Y\text{-}L\text{-}PI]_z \qquad \text{(I)}$$

wherein,
Φ is a residue of a polymerization initiator, wherein Φ is represented by general formulae (IVa) or (IVb), $$\text{Et}-O-\overset{\overset{\displaystyle O}{\|}}{C}-\underset{\underset{\displaystyle CH_3}{|}}{C}-\overset{\overset{\displaystyle O}{\|}}{C}-O-\text{Et} \qquad \text{(IVa)}$$

$$\text{Et}-O-\overset{\overset{\displaystyle O}{\|}}{C}-\underset{|}{CH}-CH_2CH_2-\underset{|}{CH}-\overset{\overset{\displaystyle O}{\|}}{C}-O-\text{Et}, \qquad \text{(IVb)}$$

M is a residue of at least one ethylenically unsaturated radically polymerizable monomer,
p represents an average number of monomer residues occurring in a block of monomer residues, p, x, and z are each individually selected such that said macro-photoinitiator has a number average molecular weight of at least 400, p is, independently for each x, an integer from 1 to 5000, x is, independently for each z, an integer from 1 to 20, z is at least 1, Y, independently for each z, is selected from S and O, L, independently for each z, is a bond or a divalent linking group comprising at least one divalent moiety selected from the group consisting of divalent organic moieties, divalent inorganic moieties, and combinations thereof, and PI, independently for each z, represents a photoinitiator residue.

27. A macro-photoinitiator comprising a polymer chain structure represented by the following general formula (I), $$\Phi\text{-}[[\text{-}(M)_p\text{-}]_x\text{-}Y\text{-}L\text{-}PI]_z \qquad (I)$$

wherein, $\Phi$ is a residue of a polymerization initiator,

M is a residue of at least one ethylenically unsaturated radically polymerizable monomer, wherein M is derived from at least one of alkyl (meth)acrylates having from 1 to 20 carbon atoms in the alkyl group, vinyl halides, vinyl esters of carboxylic acids, olefins, acrylonitrile, methacrylonitrile, N,N-di($C_1$-$C_6$ alkyl)-(meth)acrylamide, and mixtures thereof, p represents an average number of monomer residues occurring in a block of monomer residues, p, x, and z are each individually selected such that said macro-photoinitiator has a number average molecular weight of at least 400, p is, independently for each x, an integer from 1 to 5000, x is, independently for each z, an integer from 1 to 20, z is at least 1, Y, independently for each z, is selected from S and O, L, independently for each z, is a bond or a divalent linking group comprising at least one divalent moiety selected from the group consisting of divalent organic moieties, divalent inorganic moieties, and combinations thereof, and PI, independently for each z, represents a photoinitiator residue.

28. A macro-photoinitiator comprising a polymer chain structure represented by the following general formula (I), $$\Phi\text{-}[[\text{-}(M)_p\text{-}]_x\text{-}Y\text{-}L\text{-}PI]_z \qquad (I)$$

wherein, $\Phi$ is a residue of a polymerization initiator,

M is a residue of at least one ethylenically unsaturated radically polymerizable monomer, p represents an average number of monomer residues occurring in a block of monomer residues, p, x, and z are each individually selected such that said macro-photoinitiator has a number average molecular weight of at least 400, p is, independently for each x, an integer from 1 to 5000, x is, independently for each z, an integer from 1 to 20, z is at least 1, Y, independently for each z, is selected from S and O, L, independently for each z, is a bond or a divalent linking group comprising at least one divalent moiety selected from the group consisting of divalent organic moieties, divalent inorganic moieties, and combinations thereof, wherein —Y-L- is represented by the following general formula (IIIa),

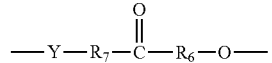

(IIIa)

wherein $R_6$ is a divalent organic moiety, and $R_7$ is a bond or a divalent organic moiety, R is —$CR_1R_2R_3$, $R_1$ is selected from hydrogen or hydroxyl, $R_2$ and $R_3$ are each independently selected from linear or branched $C_1$-$C_{20}$ alkyl, and $R_4$ in each instance is independently selected from hydrogen, and linear or branched $C_1$-$C_{20}$ alkyl, and PI, independently for each z, represents a photoinitiator residue.

* * * * *